(12) United States Patent
De Boer et al.

(10) Patent No.: US 9,695,469 B2
(45) Date of Patent: Jul. 4, 2017

(54) EXPRESSION-LINKED GENE DISCOVERY

(75) Inventors: Anne Douwe De Boer, Dreumel (NL); Michaël Johannes Marcus Ebskamp, Nieuwegein (NL); Simon Albertus Langeveld, Bennebroek (NL); Ivo Laros, Renkum (NL); Miranda Debora Van De Rhee, Rhenen (NL)

(73) Assignee: STICHTING GENETWISTER IP, Wageningen (NL)

( * ) Notice: Subject to any disclaimer, the term of this patent is extended or adjusted under 35 U.S.C. 154(b) by 1358 days.

(21) Appl. No.: 12/933,083

(22) PCT Filed: Mar. 17, 2009

(86) PCT No.: PCT/NL2009/050128
§ 371 (c)(1),
(2), (4) Date: Jan. 7, 2011

(87) PCT Pub. No.: WO2009/116863
PCT Pub. Date: Sep. 24, 2009

(65) Prior Publication Data
US 2011/0105338 A1    May 5, 2011

(30) Foreign Application Priority Data
Mar. 17, 2008   (EP) .................................... 08152859

(51) Int. Cl.
C12N 15/10    (2006.01)
C12Q 1/68     (2006.01)

(52) U.S. Cl.
CPC ....... *C12Q 1/6816* (2013.01); *C12N 15/1093* (2013.01); *C12Q 1/6827* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 2003/0099962 A1* | 5/2003 | Schernthaner et al. | 435/6 |
| 2003/0148276 A1 | 8/2003 | Li et al. | |
| 2003/0175729 A1* | 9/2003 | Van Eijk et al. | 435/6 |
| 2004/0067493 A1 | 4/2004 | Matsuzaki et al. | |
| 2005/0042654 A1 | 2/2005 | Mei et al. | |
| 2006/0084083 A1* | 4/2006 | Ruan et al. | 435/6 |
| 2010/0029498 A1* | 2/2010 | Gnirke et al. | 506/9 |

FOREIGN PATENT DOCUMENTS

| | | |
|---|---|---|
| WO | WO-02/34949 | 5/2002 |
| WO | WO-03/027258 | 4/2003 |
| WO | WO-03/050242 | 6/2003 |

OTHER PUBLICATIONS

Maget et al (FEBS Letters, 1994 vol. 351: pp. 271-275).*
Hodges et al in "Genome-wide in situ exon capture for selective resequencing." (Nat Genet 2007 vol. 39, No. 12, pp. 1522-1527. Published online Nov. 4, 2007).*
Espelund et al., Biotechniques (1992) 13(1):74-78, 80.
International Search Report for PCT/NL2009/050128, mailed on Sep. 16, 2009, 5 pages.

* cited by examiner

*Primary Examiner* — Catherine S Hibbert
(74) *Attorney, Agent, or Firm* — Morrison & Foerster LLP

(57) ABSTRACT

The invention relates to a method for analyzing a genomic region of an organism, comprising four major parts. The first part involves the isolation of mRNA from a selected organism that is used for the preparation of small single stranded DNA fragments with one adaptor containing an affinity label. These DNA fragments are used in part three. In the second part, genomic DNA from the same or a related organism is isolated. This genomic DNA is fragmented and ligated to adaptor molecules. In the third part, these genomic fragments are hybridized with single stranded DNA fragments from part one, and the hybrids formed in this process are used for synthesis of DNA fragments. These fragments will be used in part four which involves sequencing of these fragments using one of the available high throughput sequencing methods.

17 Claims, 4 Drawing Sheets

SEQUENCE LISTING

<160> NUMBER OF SEQ ID NOS: 22

<210> SEQ ID NO 1
<211> LENGTH: 11
<212> TYPE: DNA
<213> ORGANISM: Artificial
<220> FEATURE:
<223> OTHER INFORMATION: restriction site
<220> FEATURE:
<221> NAME/KEY: misc_feature
<222> LOCATION: (8)..(11)
<223> OTHER INFORMATION: n is a, c, g, or t

<400> SEQUENCE: 1
gctcttcnnn n                                                          11

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
agtccgtcgc atcgctcttc                                                 20

<210> SEQ ID NO 3
<211> LENGTH: 16
<212> TYPE: DNA
<213> ORGANISM: Artificial
<220> FEATURE:
<223> OTHER INFORMATION: primer

<400> SEQUENCE: 3
gaagagcgat gcgacg                                                     16

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
agtgggtgtc ctgggtcaac                                                 20

<210> SEQ ID NO 5
<211> LENGTH: 16
<212> TYPE: DNA
<213> ORGANISM: Artificial
<220> FEATURE:
<223> OTHER INFORMATION: primer

<400> SEQUENCE: 5
gttgacccag gacacc                                                     16

<210> SEQ ID NO 6
<211> LENGTH: 22
<212> TYPE: DNA
<213> ORGANISM: Artificial
<220> FEATURE:
<223> OTHER INFORMATION: oligonucleotide ELTD AdE Eco1

<400> SEQUENCE: 6
cttgtagggc acgggtcgag ag                                              22

```
<210> SEQ ID NO 7
<211> LENGTH: 22
<212> TYPE: DNA
<213> ORGANISM: Artificial
<220> FEATURE:
<223> OTHER INFORMATION: oligonucleotide ELTD AdE Eco2

<400> SEQUENCE: 7
aattctctcg acccgtgccc ta                                              22

<210> SEQ ID NO 8
<211> LENGTH: 22
<212> TYPE: DNA
<213> ORGANISM: Artificial
<220> FEATURE:
<223> OTHER INFORMATION: oligonucleotide ELTD AdE Hind1

<400> SEQUENCE: 8
cttgtagggc acgggtcgga ga                                              22

<210> SEQ ID NO 9
<211> LENGTH: 22
<212> TYPE: DNA
<213> ORGANISM: Artificial
<220> FEATURE:
<223> OTHER INFORMATION: oligonucleotide ELTD AdE Hind2

<400> SEQUENCE: 9
agcttctccg acccgtgccc ta                                              22

<210> SEQ ID NO 10
<211> LENGTH: 22
<212> TYPE: DNA
<213> ORGANISM: Artificial
<220> FEATURE:
<223> OTHER INFORMATION: oligonucleotide ELTD AdF Bst1

<400> SEQUENCE: 10
gaatggctgg gagagtgctg ag                                              22

<210> SEQ ID NO 11
<211> LENGTH: 22
<212> TYPE: DNA
<213> ORGANISM: Artificial
<220> FEATURE:
<223> OTHER INFORMATION: oligonucleotide ELTD AdF Bst2

<400> SEQUENCE: 11
gatcctcagc actctcccag cc                                              22

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
gtagggcacg ggtcggagaa gc                                              22

<210> SEQ ID NO 13
<211> LENGTH: 489
<212> TYPE: DNA
<213> ORGANISM: Malus domestica
```

<220> FEATURE:
<221> NAME/KEY: misc_feature
<222> LOCATION: (445)..(445)
<223> OTHER INFORMATION: n is a, c, g, or t

<400> SEQUENCE: 13

| | | | | | | |
|---|---|---|---|---|---|---|
| tatgttgtga | taaccatatg | gcttccctga | catgctctga | acatactccc | atgctgcagt | 60 |
| agagttgaat | tttgcacgca | cctctggatg | caagggaagc | aaggctattt | gtggattaga | 120 |
| actatccttg | agtgtcaact | cccaccactc | atcccatgga | atcaccgcta | taatttcttc | 180 |
| accctgcaat | attaaattat | taataaatgt | aaaaatcaac | caaaagaaa | agaactaacc | 240 |
| acaataaact | ctacaaaaaa | gaaagaact | aaagcaaagt | ttaaaataat | taagaaatct | 300 |
| gtgcaagatt | gtcatatatt | taattttgtc | cctaaacaaa | cgctcatcat | atgttcatca | 360 |
| ctacaatcct | gattcaacta | ttattccact | aaaggcaaag | aaccaaaaca | tttagcttaa | 420 |
| tttctattcc | taataaatcc | caaanacatg | aaatgagttg | cttgcataag | catatactca | 480 |
| attgaaaat | | | | | | 489 |

<210> SEQ ID NO 14
<211> LENGTH: 352
<212> TYPE: DNA
<213> ORGANISM: Malus domestica

<400> SEQUENCE: 14

| | | | | | | |
|---|---|---|---|---|---|---|
| cagcgacctg | tttacgtgca | aggtttggat | ggaagagatt | gaacagtgat | gccaaattga | 60 |
| attgcctcca | gaacaaatct | gaagggtgca | aaaaacatgt | acttttttgag | agttgaagaa | 120 |
| tgacgacact | ttcttatgtt | ctatattatc | ttggttaagt | tttttgcagg | acggaatgaa | 180 |
| tcctcgtctt | tttttttccct | atcaaaaaga | agaaagctga | gttttatgt | ttgatgtctt | 240 |
| gatgatggat | gacctagtgt | tcaagtgaaa | aattcgacgg | acaaaacgct | tggcaatcca | 300 |
| atttgtgccg | tgtataatgt | gtcacgtcca | aacgagtttc | acatcgaaga | aa | 352 |

<210> SEQ ID NO 15
<211> LENGTH: 867
<212> TYPE: DNA
<213> ORGANISM: Malus domestica
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (196)..(198)
<223> OTHER INFORMATION: n is a, c, g, or t

<400> SEQUENCE: 15

| | | | | | | |
|---|---|---|---|---|---|---|
| tgttattgtt | tcattgaaac | ataacgttac | ataacaatat | aggnnncatt | tggaacaact | 60 |
| tttaaaatgg | ctgaaaacgc | attttgtgaa | aatgattttt | aaacagtttt | gagtaaaaat | 120 |
| acaatgaatc | atagaaaagt | acttgaaatg | ctttctacaa | atagcatata | actagtgctt | 180 |
| atttcaaaaa | atattnnnaa | aacataaaca | aaattctcta | aaaatattta | cggtcattgt | 240 |
| aaaatcattt | tcaaacgtga | ttataatcag | gctatgtaaa | atattctta | atattgactc | 300 |
| aacaataaac | ggcgaatcga | aacgatacac | ggagtggagc | gtgggagatg | ggaggaaagg | 360 |
| atcaccgcac | gcaatcaaag | agtgcattcg | cagccgtcag | atgatgataa | aaatgatggg | 420 |
| tgtgctctct | cgacaacgca | cacatgccac | gtaaacgcaa | aacgaacatt | gcacaattac | 480 |
| taaattgcca | ccgatggaga | gccgccctc | cctaatccca | tctcagtcaa | atcccttgtt | 540 |

```
gactgtgcgc ctctctctct ctctctctct ctctcctctc tctttctctc tcttcaattc    600
ctcgctcatc atttctatat aaaacccaca gcctgcctcc tagtcctcca tcgccatctc    660
cacaccgtt tctctcacat attttctgca gccaaacact ctttccaccc aaacactaca    720
tacacaaaac gccaccgttt agttatggcg ccgagagaga agacggccac cgccgccgtt    780
aggatgaacg gtaacggaaa cgtgaaggag gtgcatttta gaggtgtgag gaagaggccg    840
tgggggaggt acgccgccga gatcaga                                        867
```

<210> SEQ ID NO 16
<211> LENGTH: 600
<212> TYPE: DNA
<213> ORGANISM: Arabidopsis thaliana

<400> SEQUENCE: 16

```
cgaagattcg aggtagatgg ggtggttttg agacgttaga gaaatgggtg actggggctt     60
ttgctggtca tactgctgtt tgtttgaagg atgatttggg gaatctttgg gttggtgaat    120
caggacatga gaacgaaaag gtagacctaa acattttgaa gttagtggat agaaagagag    180
atatttact atcttttccc ccataggggtg aagaaatcat tgttgtgatc ccttgggatg    240
aatggtggga gctgactttg aaggataatt caaatcctca gtagctttg cttcctctac    300
atcctgatat ccgggcaaag ttcaacaata ctgctgcgtg gaatatgca cggagtatgt    360
tgggcaaacc gtatggatat cacaacatga tattcagctg gatcgacact ctaggcgata    420
actacccccc tcccccttgat gctcacttgg tactttttaa tccctgatat tcttaaagat    480
ctatcatcat taagatcatc atggtaatca acaagccaca ttgaactttc aggttatttc    540
tgtcatgtct atgtggactc gtgtacaacc tgcatatgct gctaatatgt ggaacgaggc    600
```

<210> SEQ ID NO 17
<211> LENGTH: 219
<212> TYPE: DNA
<213> ORGANISM: Malus domestica

<400> SEQUENCE: 17

```
gcatccagag gtgcgtgcaa aattcaactc tactgcagca tgggagtatg ttcggagcat     60
gtcagggaag ccatatggtt atcacaacat gatatttagc tggattgaca ccatggccga    120
caactttcct cctcctcttg atactcactt ggttgtttca gtcatgtcta tgtggaccag    180
aatgcagcct gcatatgctg caaatatgtg gaatgaggc                           219
```

<210> SEQ ID NO 18
<211> LENGTH: 379
<212> TYPE: DNA
<213> ORGANISM: Malus domestica

<400> SEQUENCE: 18

```
agttgaatca ggattgtagt gatgaacata tgatgagcgt ttgtttaggg acaaaattaa     60
atatatgaca atccttgcaca gatttcttaa ttattttaaa ctttgcttta gttcttttct    120
tttttgtaga gttattgtg gttagttctt ttcttttttgg ttgattttta catttattaa    180
taatttaata ttgcagggtg aagaaattat agcggtgatt ccatgggatg agtggtggga    240
gttgacactc aaggatagtt ctaatccaca aatagccttg cttcccttgc atccagaggt    300
gcgtgcaaaa ttcaactcta ctgcagcatg ggagtatgtt cagagcatgt cagggaagcc    360
atatggttat cacaacata                                                  379
```

```
<210> SEQ ID NO 19
<211> LENGTH: 352
<212> TYPE: DNA
<213> ORGANISM: Malus domestica

<400> SEQUENCE: 19
cagcgacctg tttacgtgca aggtttggat ggaagagatt gaacagtgat gccaaattga      60
attgcctcca gaacaaatct gaagggtgca aaaacatgt acttttttgag agttgaagaa     120 tgacgacact ttcttatgtt ctatattatc ttggttaagt tttttgcagg acggaatgaa    180
tcctcgtctt tttttccct atcaaaaaga agaaagctga gttttttatgt ttgatgtctt    240 gatgatggat gacctagtgt tcaagtgaaa aattcgacgg acaaaacgct tggcaatcca    300
atttgtgccg tgtataatgt gtcacgtcca aacgagtttc acatcgaaga aa            352

<210> SEQ ID NO 20
<211> LENGTH: 567
<212> TYPE: DNA
<213> ORGANISM: Malus domestica

<400> SEQUENCE: 20
aacaataaac ggcgaatcga aacgatacac ggagtggagc gtgggagatg ggaggaaagg      60
atcaccgcac gcaatcaaag agtgcattcg cagccgtcag atgatgataa aaatgatggg    120
tgtgctctct cgacaacgca cacatgccac gtaatacgga aacgaacatt gcacaattac    180
taaattgcca ccgatggaga gccgcccctc cctaatccca tctcagtcaa atcccttgtt    240
gactgtgcgc ctctctctct ctctctctct ctctcctctc tctttctctc tcttcaattc    300
ctcgctcatc atttctatat aaaacccaca gcctgcctcc tagtcctcca tcgccatctc    360 cacaccgtt tctctcacat attttctgca gccaaacact ctttccaccc aaacactaca    420
tacacaaaac gccaccgttt agttatggcg ccgagagaga agacggccac cgccgccgtt    480
aggatgaacg gtaacggaaa cgtgaaggag gtgcatttta gaggtgtgag gaagaggccg    540
tgggggaggt acgccgccga gatcaga                                         567

<210> SEQ ID NO 21
<211> LENGTH: 238
<212> TYPE: DNA
<213> ORGANISM: Malus domestica

<400> SEQUENCE: 21
cacccgtttc tctcacatat tttctgcagc caaacactct ttccacccaa acactacata      60
tacaaaacgc caccgtttag ttatggcgcc gagagagaag acggccaccg ccgccgttag    120
gatgaacggt aacggaaacg tgaaggaggt gcattttaga ggtgtgagga agaggccgtg    180 gggaggtac gccgccgaga tcagagatcc cggcaagaag agccgggtct ggctcgga      238

<210> SEQ ID NO 22
<211> LENGTH: 234
<212> TYPE: DNA
<213> ORGANISM: Malus domestica

<400> SEQUENCE: 22
cagcgacctg tttacgtgca aggtttggat ggaagagatt gaacagtgat gccaaattga      60
attgcctcca gaacaaatct gaagggtgca aaaacatgt acttttttgag agttgaagaa     120 tgacgacact ttcttatgtt ctatattatc ttggttaagt tttttgcagg acggaatgaa    180
tcctcgtctt tttttccct atcaaaaaga agaaagctga gttttttaaaa aaaa          234
```

EXPRESSION-LINKED GENE DISCOVERY

CROSS-REFERENCE TO RELATED APPLICATIONS

This application is the national phase of PCT application PCT/NL2009/050128 having an international filing date of 17 Mar. 2009, which claims benefit of European application No. 08152859.8 filed 17 Mar. 2008. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 313632010200Seqlist.txt | Dec. 29, 2010 | 9,359 bytes |

The invention relates to the field of molecular biology and biotechnology, more specifically to the field of sequencing, detection and identification of nucleic acid sequences in genomic DNA. More in particular, the invention relates to the application of a method in the identification of and/or detection of nucleotide sequences which represent the majority of transcribed regions and its surroundings in a genome and which are related to a wide variety of genetic traits, genes and combinations thereof. The invention can be used in the field of high throughput detection and identification of molecular markers from any origin, be it plant, animal, human, artificial or otherwise.

Breeding technologies have evolved from simple selection of visible traits into advanced methods for detection of multigenic traits using molecular markers. In principal, each genetic difference between different lines of a crossing population can represent an altered trait. However due to the complexity of most genomes it is not possible to identify every difference that exists between genomes and to link it to a particular trait. In theory, sequencing complete genomes would reveal all differences between genomes. However, this cannot be realized practically, time and cost effectively with current sequencing technologies. Therefore, methods for detection of genetic differences have mainly been based on the principle of complexity reduction involving sequencing of a limited but fully defined part of the genomic DNA from different individuals. With the advancements in sequencing technologies complexity reduction has become less important for certain applications like analysis of transcriptomes that represent all expressed gene sequences. The size of eukaryotic genomes ranging from a few tens to several hundreds of megabases is nevertheless still beyond the capacity of current high throughput sequencing technologies. Furthermore, the vast majority of genomic DNA in eukaryotic organisms, especially those with larger genome sizes, provides no valuable information for breeding purposes as it is never expressed and therefore does not seem to contribute to expression of traits.

Therefore, to identify molecular markers, methods that focus on those parts of a genome that are more prone to reveal molecular markers closely linked to traits have an advantage over methods which analyse just random selections from genomes including non-expressed areas. This problem becomes more prominent when genome size increases. The method described makes it possible to determine sequences in a selected part of the genomic DNA representing the coding regions of the majority of expressed genes and their surroundings. Comparison of such selected parts between different individuals allows identification of polymorphic sites that are inside or in close vicinity of expressed genes. Since frequency of polymorphisms is higher in non-coding regions, more polymorphisms can be related to expressed genes as with current technologies. Also large non-coding regions surrounding more conserved genes can be analysed for the presence of polymorphisms. This may ultimately result in the discovery of at least one marker per trait. The method of the invention makes it possible to focus on SNP detection in gene encoding areas and gene regulatory areas by enlightening well defined parts of the genome among different individuals and organisms, even in organisms with complex and large genomes.

Nucleotide sequence polymorphisms, like SNPs are widely applied to construct genome maps. After polymorphisms have been linked to phenotypes in a process called genetic mapping, such polymorphisms can be used as markers in marker assisted breeding technologies to detect a particular phenotype at any stage of development. Nucleotide sequence polymorphisms are generally identified in genomic DNA. As genome sizes of all eukaryotic organisms are far exceeding the number of nucleotides that can be analysed with current high throughput sequencing technologies, reproducible procedures for complexity reduction are needed to analyse selected parts of whole genomes for finding genetic differences between individuals that can be used for genomic mapping. However, the statistical nature of complexity reduction methods which are currently applied, implies that these methods do not reveal a priori those genetic differences that can be linked to single phenotypes or are map closely to genes which contribute to a particular phenotype.

Current technologies strongly focus on discovery of single nucleotide polymorphisms (SNPs) for several reasons: SNPs are more frequently present in genomes than any other type of polymorphism, SNPs allow accurate detection of homozygous and heterozygous alleles, SNPs can be applied in high throughput applications and many industrial platforms are available which make SNP detection at any desired scale of application cost effective.

Although SNP discovery would be the method of choice in situations where low levels of polymorphism occur, like conserved genes encoding areas and genomes of closely related individuals, using EST banks for SNP discovery in individuals that are closely related may be less effective because of an inherently low level of polymorphism.

In conclusion, an SNP discovery method should ideally reveal all present SNPs that are physically linked to traits of interest, but should not be impeded by the lower levels of polymorphisms as they occur in gene encoding areas of the genome or be impeded by any requirement for knowledge of genome sequences.

Thus there is a need for a method that can reproducibly determine concomitantly sequences in areas of genomic DNA that represent the majority of gene coding regions and their surrounding regions, this without prior knowledge of genome or transcriptome sequences

SUMMARY OF THE INVENTION

The current inventors now have found a method for analysing a genomic region of an organism, comprising four major parts.

The first part involves the isolation of mRNA from a selected organism that is used for the preparation of small single stranded DNA fragments with one adaptor containing an affinity label. These DNA fragments are used in part three. In the second part genomic DNA from the same or a related organism is isolated. This genomic DNA is fragmented and ligated to adaptor molecules. In the third part these genomic fragments are hybridized with single stranded DNA fragments from part one and the hybrids formed in this process are used for synthesis of DNA fragments. These fragments will be used in part four, which involves sequencing of these fragments using one of the available high throughput sequencing methods.

Said method for the identification of genomic DNA in a sample thus comprises the steps of:
 a) isolation and purification of mRNA from tissue samples of an organism;
 b) synthesis of cDNA using said mRNA as a template;
 c) optionally complexity reduction of said cDNA;
 d) fragmentation of said cDNA;
 e) optionally size selection of said fragments;
 f) optionally removing polyA-containing fragments by binding to streptavidin-coated affinity beads;
 g) polishing of said fragments of cDNA;
 h) ligation of said fragments with one adaptor comprising a recognition site for a rare restriction enzyme and another adaptor containing a biotin label;
 i) optionally size selection of said fragments;
 j) nick repair of said fragments;
 k) selection of said fragments that contain both adaptor sequences;
 l) amplification of said fragments using primers annealing to the adaptor sequences described in step h, wherein one primer is complementary to the adaptor with a rare restriction site and the other primer contains a biotin label.
 m) binding said fragments to streptavidin-coated affinity beads;
 n) removing adaptors containing the rare restriction site using the corresponding restriction enzyme from said fragments;
 o) removing single strands not attached to affinity beads by a biotin-streptavidin interaction from double stranded DNA fragments attached to affinity beads;
 p) isolation and purification of genomic DNA for example from the organism of step a
 q) fragmentation of said genomic DNA;
 r) optionally polishing of said genomic DNA;
 s) ligation of said genomic DNA with one single type of adaptor or with two different type of adaptors;
 t) melting out of said genomic DNA into single stranded DNA;
 u) hybridizing genomic DNA from step t) with cDNA on beads from step o);
 v) remove unbound genomic DNA by washing;
 w) extension of the cDNA-genomic DNA hybrid by a polymerase to create a double-stranded template;
 x) performing PCR on said genomic DNA-cDNA hybrid
 y) selection of fragments larger than about 100 basepairs from said PCR;
 z) optionally purification of said fragments and
 aa) high throughput sequencing of said fragments.

In another embodiment, the method is extended to a method for identifying polymorphisms, comprising all the steps of the method according to claim and additionally comparing sequence data from two or more samples to identify polymorphisms.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982)). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

SNP: A single nucleotide polymorphism is a DNA sequence variation occurring when a single nucleotide—A, T, C, or G—in the genome differs between members of a species (or between paired chromosomes in an individual) at a specific locus. SNPs are the most common type of genetic variation. SNPs may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed synonymous and if a different polypeptide sequence is produced it is termed non-synonymous. As SNPs are evolutionarily conserved, they can be used as markers for quantitative trait loci (QTL) analysis and in association studies.

Intron: Introns are non-coding sections of a gene that are removed from pre-mRNAs in a process named splicing to produce functional mRNAs.

Exon: An exon is any region of DNA within a gene that is transcribed to the final messenger RNA (mRNA) molecule, rather than being spliced out from the transcribed RNA molecule like introns.

cDNA: cDNA is an artificial form of DNA synthesized by the reverse transcriptase enzyme using RNA molecules as a template.

Genomic DNA: the term genomic DNA indicates that the DNA is derived from the situation 'as is'. This means that genomic DNA harbors sequences, as they will be found in nature, e.g., including introns and regulatory sequences. Genomic DNA can be derived from different sources, like chromosomes, but also from extrachromosomal sources such as mitochondria, chloroplasts and plasmids.

Cot-1 DNA: The technique that is used to determine the sequence complexity of any genome involves the denaturation and renaturation of DNA. DNA is denatured by heating and this melts the H-bonds and renders the DNA single-stranded. If the DNA is rapidly cooled, the DNA remains single-stranded. But if the DNA is allowed to cool slowly, sequences that are complementary will find each other and eventually base pair again. The rate at which the DNA reanneals (another term for renatures) is a function of the species from which the DNA was isolated, also identified as the "Cot" curve. DNA that has a high Cot value is highly repetitive DNA, while DNA with a low Cot value is only available in low copies or is unique. In the method we use DNA with a Cot value of 1, a fraction of total genomic DNA that is enriched for highly repetitive DNA sequences.

Annotation: annotation of cDNA sequences comprises two steps. The obtained sequences are compared to nucleotide and/or amino acid sequences as available in (public) databases. Methods for alignment of sequences for comparison purposes are well known in the art. This comparison is typically performed with help of a program such as the NCBI Basic Local Alignment Search Tool (BLAST) describe by Altschul, et al., (1990). This program is available from several sources including the National Center for Biological Information (NCBI, Bethesda, Md.) and on the internet at the World Wide Web address ncbi.nlm.nih.gov/BLAST. This program compares the identified cDNA/EST (Expressed Sequence Tags) sequences with the sequences present in databases and presents the results based on a certain score and a probability parameter. The program can select those cDNA/EST sequences with a certain predetermined lower limit of said probability parameter. The selected cDNA/EST sequences are then in a second step provided with an annotation (i.e., a link to a sequence as present in a database). This kind of annotation is called an "electronic annotation".

Clustering: with the term "clustering" is meant the building of a collection of sequences with similarity through pairwise comparison of two or more nucleotide sequences and selection on the presence of short or long stretches of identical or similar nucleotides. Several methods for alignment of nucleotide sequences are known in the art, as will be further explained below. Sometimes the terms "assembly" or "alignment" are used as synonyms.

Identifier: a short sequence that can be added to an adaptor or a primer or included in its sequence or otherwise used as label to provide a unique identifier. Such a sequence identifier can be a unique base sequence of varying but defined length uniquely used for identifying a specific nucleic acid sample. For instance 4 bp tags allow 4(exp4)=256 different tags. Typical examples are ZIP sequences, known in the art as commonly used tags for unique detection by hybridization (Iannone, et al., *Cytometry* (2000) 39:131-140). Using such an identifier, the origin of a PCR sample can be determined upon further processing. In the case of combining processed products originating from different nucleic acid samples, the different nucleic acid samples are generally identified using different identifiers.

Sequencing: As has also been disclosed in WO 2006/137733, the term sequencing refers to determining the order of nucleotides (base sequences) in a nucleic acid sample, e.g., DNA or RNA.

The term high-throughput screening, often abbreviated as HTS, is a method for scientific experimentation especially relevant to the fields of biology and chemistry where, through a combination of modern robotics and other specialized laboratory hardware, it allows a researcher to effectively screen large amounts of samples simultaneously. In the present invention, more specifically, this is a sequencing technology such as disclosed herein elsewhere (from 454 Life Sciences, on the World Wide Web at 454.com and Illumina, at illumina.com), e.g., the Illumina Solexa sequencing approach relies on attachment of randomly fragmented genomic DNA to a planar, optically transparent surface and solid phase amplification to create an ultra-high density sequencing flow cell with >10 million clusters, each containing ~1,000 copies of template per sq. cm. These templates are sequenced using a robust four-color DNA sequencing-by-synthesis technology that employs reversible terminators with removable fluorescence. This approach ensures high accuracy and avoidance of artifacts with homopolymeric repeats. High sensitivity fluorescence detection is achieved using laser excitation and total internal reflection optics.

The following definitions in italics have been obtained from WO 2006/137733 (applicant: KeyGene B. V., inventors: M. J. T. Van Eijk, H. J. A. Van der Poel, agent: R. J De Lang of Exter Polak & Charlouis B. V.).

Restriction endonuclease: a restriction endonuclease or restriction enzyme is an enzyme that recognizes a specific nucleotide sequence (target site) in a double-stranded DNA molecule, and will cleave both strands of the DNA molecule at or near every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or, desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g., about 10 to about 30 base pairs in length, which are designed such that they can be ligated to the ends of restriction fragments. Adaptors are generally composed of two synthetic oligonucleotides that have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors). Specifically, in the present invention an adaptor is a double-stranded DNA molecule, usually between 15 and 60 base pairs, which can be prepared by annealing of two (partially) complementary oligonucleotides. The adaptors used herein can be blunt-ended, or have a specific overhang for ligation to DNA molecules with a complementary overhang, such as those created by restriction endonuclease digestion. The adaptors can have an additional, non-compatible overhang on the other end, which cannot ligate to a blunt-ended DNA fragment and not to DNA with a specific overhang created by a type II restriction endonuclease, thereby preventing the ligation of multiple adaptors with each other.

The adaptors provide annealing sites for primers during PCR to amplify the different DNA fragments ligated to the adaptors in a single PCR reaction.

One of the adaptors ligated to the cDNA molecules can carry a type IIs restriction endonuclease recognition sequence to cleave the adaptor off the cDNA molecule once bound to the solid phase.

Adaptor-ligated restriction fragments: restriction fragments that have been capped by adaptors.

Primers: in general, the term primers refer to DNA strands, which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules that are used in a polymerase chain reaction (PCR) as primers.

DNA amplification: the term DNA amplification will be typically used to denote the in vitro synthesis of double-stranded DNA molecules using PCR or a comparable amplification system. It is noted that other amplification methods exist and they may be used in the present invention. Methods of the invention can in principle be performed by using any nucleic acid amplification method, such as the Polymerase Chain Reaction (PCR; Mullis 1987, U.S. Pat. Nos. 4,683, 195, 4,683,202, and 4,800,159) or by using amplification reactions such as Ligase Chain Reaction (LCR; Barany, *Proc. Natl. Acad. Sci. USA* (1991) 88:189-193; EP Appl. No. 320,308), Self-Sustained Sequence Replication (3SR; Guatelli, et al., *Proc. Natl. Acad. Sci. USA* (1990) 87:1874-1878), Strand Displacement Amplification (SDA; U.S. Pat. Nos. 5,270,184, and 5,455,166), Transcriptional Amplification System (TAS; Kwoh, et al., *Proc. Natl. Acad. Sci. USA* (1989) 86:1173-1177), Q-Beta Replicase (Lizardi, et al., *Bio/Technology* (1988) 6:1197), Rolling Circle Amplification (RCA; U.S. Pat. No. 5,871,921), Nucleic Acid Sequence Based Amplification (NASBA), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of DNA.

In order to amplify DNA with a small number of mismatches to one or more of the amplification primers, an amplification reaction may be performed under conditions of reduced stringency (e.g., a PCR amplification using an annealing temperature of 38° C., or the presence of 3.5 mM MgCl2). The person skilled in the art will be able to select conditions of suitable stringency.

Polishing (also called end repair) refers to the conversion of non-blunt ended DNA into blunt ended DNA.

Polishing digestion of genomic DNA (gDNA) templates with DNase I in the presence of Mn2+ produces fragments of DNA that are either blunt-ended or have protruding termini with one or two nucleotides in length. Similarly, fragmentation of DNA by mechanical means provides a combination of fragments with blunt-ends or overhanging ends. These DNA fragments, whether generated enzymatically or mechanically, may be "polished" using the procedure described below.

In one method, polishing may be performed by treatment of 3'-overhanging fragments with a single strand-specific exonuclease, such as BAL32 nuclease or Mung Bean nuclease. Generally, the nuclease should be calibrated prior to use.

In another method, blunt ends are created with Pfu DNA polymerase or with other DNA polymerases such as T4 DNA polymerase or Klenow DNA polymerase. Pfu "polishing" or blunt ending can be used to increase the amount of blunt-ended species generated following genomic template digestion with DNase I. Pfu DNA polymerase fills in 5' overhangs. Additionally, Pfu DNA polymerase exhibits 3' to 5' exonuclease activity. Thus, the enzyme can be used to remove single and double nucleotide extensions to further increase the amount of blunt-ended DNA fragments available for adaptor ligation (see, e.g., Costa, G. L. and M. P. Weiner, Protocols for cloning and analysis of blunt-ended PCR-generated DNA fragments. *PCR Methods Appl* (1994) 3(5):595; Costa, G. L., A. Grafsky and M. P. Weiner, Cloning and analysis of PCR-generated DNA fragments. *PCR Methods Appl* (1994) 3(6):338; Costa, G. L. and M. P. Weiner, Polishing with T4 or Pfu polymerase increases the efficiency of cloning of PCR products. *Nucleic Acids Res.* (1994) 22(12):2423).

The present inventors have found that by providing the genomic DNA and by using adaptor-ligated cDNA derived fragments to act as primers for amplification of genomic DNA fragments, it appears possible to detect genome sequences outside regions that are actually transcribed, i.e., the promoter, intron and terminator sequences. It thus combines the possibility of rapid identification of genomic DNA fragments in expressed regions of the genome, wherein multiple samples can be sequenced in a single run, with the possibility to study surrounding genomic DNA fragments of these regions and the possibility to detect genetic variation in gene encoding fragments, intron fragments and fragments covering regulatory genome sequences.

A further advantage is that the method of the invention is generally applicable, i.e., for all organisms. No information on the genome or genomic organization is needed beforehand. Another advantage is that no cloning step is required in the present method. This enables the sequencing of sequences coding for toxic substances or for regulatory proteins, which otherwise would be impossible because the host organism in which such sequences would be cloned and expressed would not or hardly survive. In the same sense also sequences that would create problems in cloning can now be approached and there is no limit as to the length of the sequences, which also may cause problems in cloning schedules.

A further advantage is that the current method does not require full length cDNA, but may be used with shorter sequences. This is especially useful when analyzing large genomes (e.g., from bulbous plants) since then a focus on the most interesting or relevant regions of the genome can be maintained.

A next advantage is that it is possible with the current method to generate primers for all expressed DNA sequences, which means that it is possible to obtain the genomic data from the expressed sequences.

DETAILED DESCRIPTION OF THE INVENTION

Figure 1:
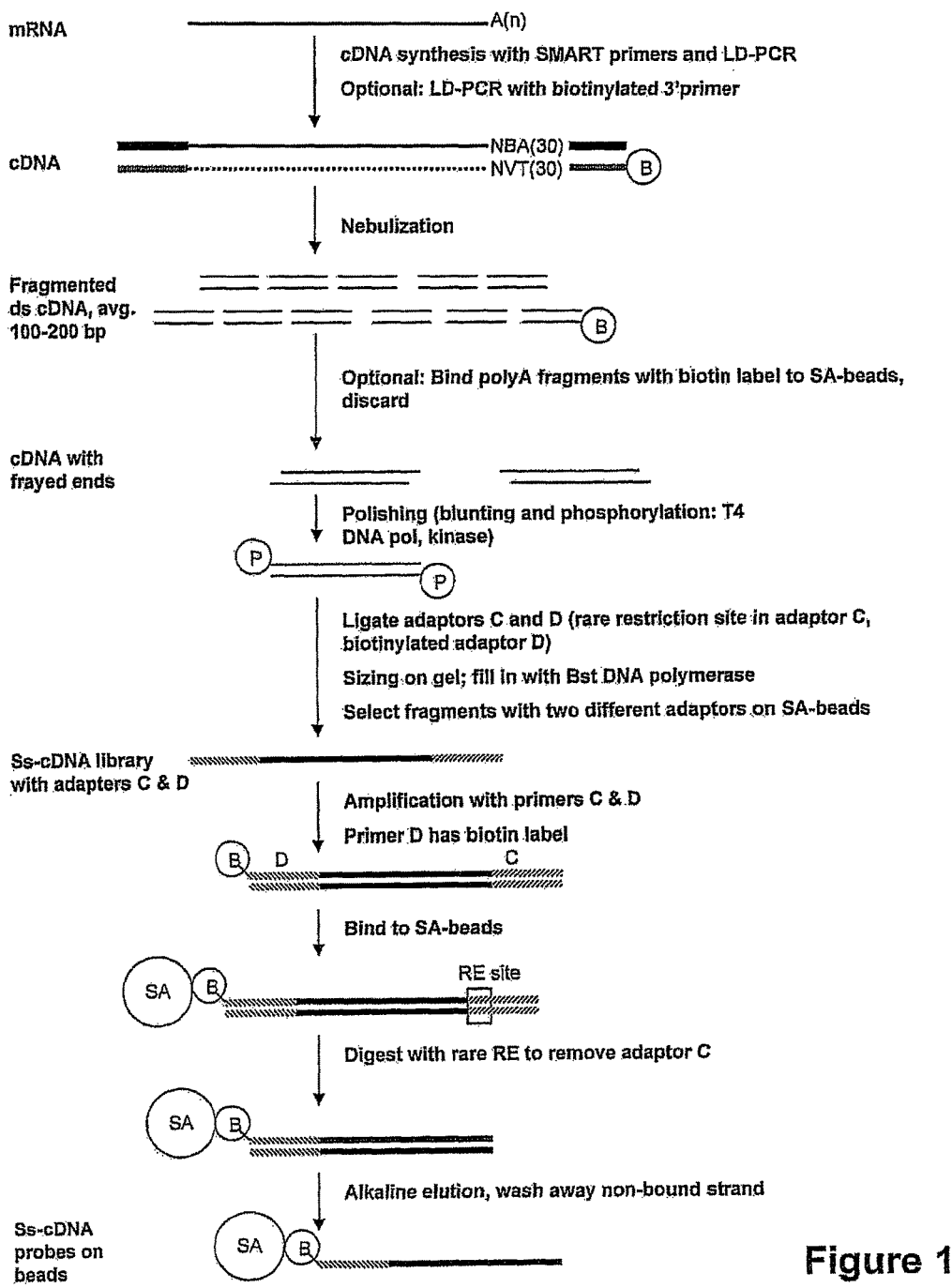
FIG. 1. Schematic representation of creation of small single stranded DNA molecules from mRNA. C is an adaptor, D is a different adaptor, B is biotin, P is a phosphate group, by is base pairs, ds is double stranded, ss is single stranded, RE is a restriction enzyme, SA is streptavidin, LD-PCR is long distance PCR, $NBA_{(30)}$ and $NVT_{(30)}$ are single-letter code for nucleotides according the Nomenclature Committee of the International Union of Biochemistry (NC-IUB) syntax rules for nucleotides, $A_{(30)}$ and $T_{(30)}$ indicate stretches of 30 As and 30 Ts respectively.
Figure 2:
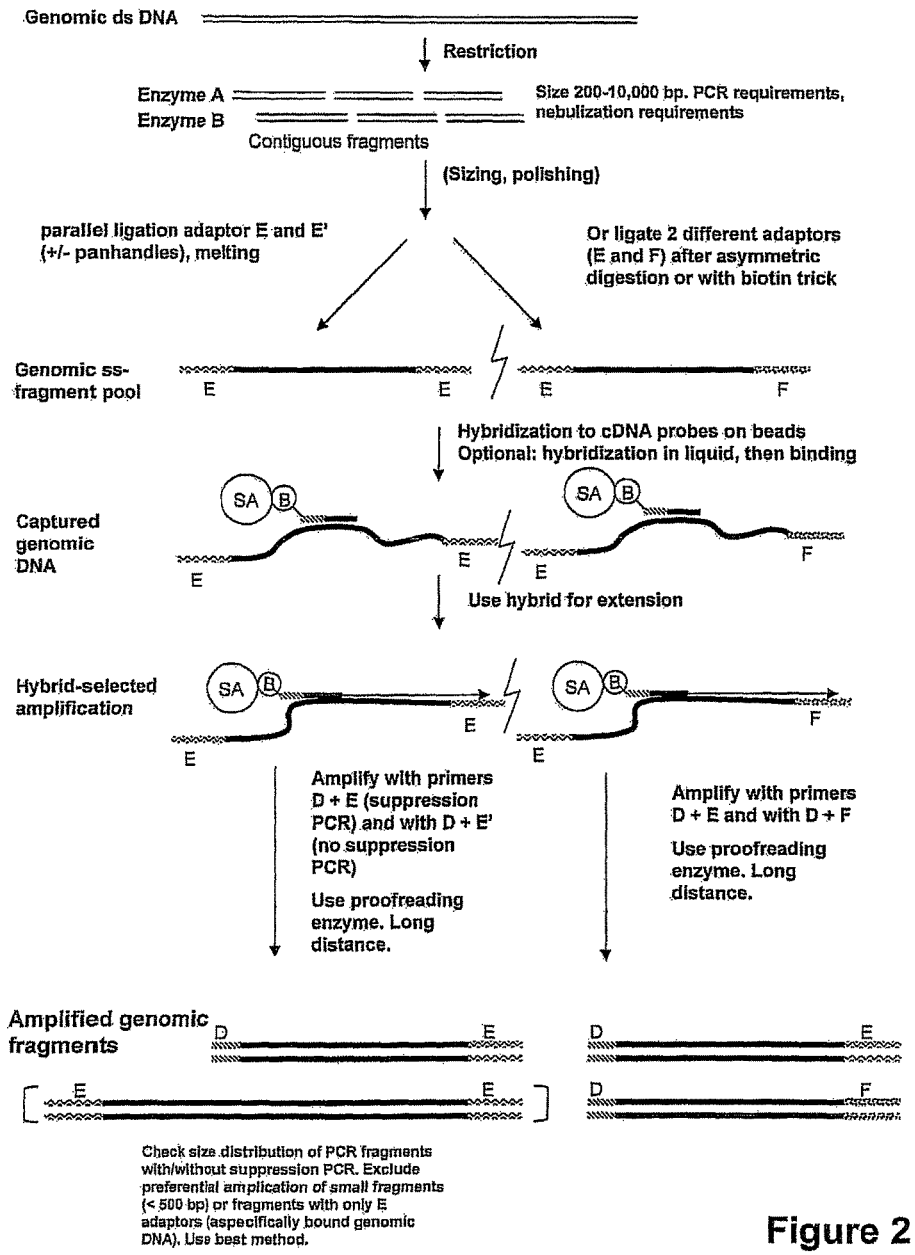
FIG. 2. Schematic representation of creation of fragments of genomic DNA and the subsequent hybridization with small single stranded DNA molecules from mRNA (FIG. 1). After several steps, DNA fragments are obtained that can be sequenced using high throughput sequencing methods. C and D are adaptors also depicted in FIG. 1. E and F are different adaptors, B is biotin, by is base pairs, ds is double strand, ss is single strand and SA is streptavidin.

In one aspect, the invention relates to a method for the identification of genomic DNA in a sample comprising of 4 different parts.

Part 1.

In this part small sequences are generated from cDNA that will be used as priming sequences in part 3. The part consists of the following steps:

a) isolation and purification of mRNA from tissue samples of an organism;

b) synthesis of cDNA using said mRNA as a template;

c) optionally complexity reduction of said cDNA;

d) fragmentation of said cDNA;

e) optionally size selection of said fragments;

f) optionally removing polyA-containing fragments by binding to (streptavidin-coated) affinity beads;

g) polishing of said fragments of cDNA;

h) ligation of said fragments with a first adaptor comprising a recognition site for a rare restriction enzyme and a second adaptor containing a biotin label;

i) optionally size selection of said fragments;

j) nick repair of said fragments;

k) selection of said fragments that contain both adaptors sequences;

l) amplification of said fragments using primers annealing to the adaptor sequences described in step h; one primer complementary to the adaptor with the rare restriction site and the other primer containing a biotin label.

m) binding said fragments to streptavidin-coated affinity beads;

n) removing adaptors containing the rare restriction site from said fragments using the corresponding restriction enzyme;

o) removing single strands not attached to affinity beads by a biotin-streptavidin interaction from the double stranded DNA fragments attached to affinity beads.

This step results in single strands of DNA bound to streptavidin affinity beads;

Part 2:

p) isolation and purification of genomic DNA for example from the organism of step a);

q) fragmentation of said genomic DNA;

r) optionally polishing of said genomic DNA;

s) ligation of said genomic DNA with one single type of adaptor or with two different type of adaptors (preferred));

t) melting out of said genomic DNA into single stranded DNA

Part 3:

u) hybridizing genomic DNA from step t) with cDNA on beads from step o);

v) remove unbound genomic DNA by washing w) extension of the cDNA-genomic DNA hybrid by a polymerase to create a double-stranded template x) performing PCR on said genomic DNA-cDNA hybrid y) selection of fragments larger than about 100 basepairs from said PCR by size fractionation z) optionally purification of said fragments Part 4 aa) Use the fragments obtained in step z) for high throughput sequencing according to manufacturer.

Additionally, when the sequence of the genomic DNA has been determined a step can follow to identify changes in the sequences of two or more samples:

ab) Comparing the data of two or more sample to identify polymorphisms.

By treating a sample nucleic acid in this way it is possible to analyse reproducibly genomic regions of an organism covering gene encoding and connected regions, without having any information about the structure or content of the genome of the organism. When the sequencing protocol allows for adaptors with identifiers, multiple samples can be combined in a single sequencing run.

The method starts with the isolation and purification of a sample of mRNA from an organism. Obtaining a sample of mRNA in this way is a routine procedure nowadays.

Similarly for the next step, wherein—with the aid of the enzyme reverse transcriptase—a DNA copy, the so called cDNA is made from the RNA in the sample. This cDNA comprises the transcriptome of the cell from which the RNA has been derived, representing the total of genetic information that has been transcribed at the moment that the sample was taken. Thus, depending on the cell type, the tissue from which the cell was derived, the age of the cell, the developmental phase of the cell and environmental conditions, the transcriptome of each cell of the same organism will differ, and even from the same cell, when sampled at different times and/or different conditions, different transcriptomes would be obtained. The nucleic acid in the original sample will usually be in the form of mRNA. However, also RNA or DNA derived from other sources can be useful, such as RNA or DNA derived from gene libraries The nucleic acid in the sample may be double stranded, single stranded, and double stranded DNA denatured into single stranded DNA. The sample can be from any organism, whether plant, animal, synthetic or human. It will be understood that if a DNA sample is obtained, no reverse transcriptase reaction is needed.

Since the sample, if it is derived from whole cell mRNA, contains the total transcriptome, sometimes it would be desirable to retrieve only a subset of it. This can be achieved in several ways: one possible way is to discriminate on size of the cDNA, e.g., by ultraspeed centrifugation. The principle underlying this method is known as complexity reduction. Other options for complexity reduction are for example hybridization methods which select for abundant or non-abundant transcripts or for example methods for capturing specific transcripts either to remove them from the pool of cDNA molecules or to select them for further analysis or for example methods like cDNA-AFLP that create a subset of the pool of cDNA molecules by restriction digestion.

Once the desired sample of cDNA has been obtained, the cDNA is fragmented, which can be done enzymatically or mechanically. The nucleic acid sample is digested with at least one restriction endonuclease to provide a set of restriction fragments. In certain embodiments, two or more endonucleases can be used to obtain restriction fragments. The endonuclease can be a frequent cutter (a recognition sequence of 3-5 bp, such as Mse1) or a rare cutter (recognition sequence of >5 bp, such as EcoRI). In certain preferred embodiments, a combination of a rare and a frequent cutter is preferred. In certain embodiments, in particular when the sample contains or is derived from a relatively large genome, it may be preferred to use a third enzyme (rare or frequent cutter) to obtain a larger set of restriction fragments of shorter size.

As a restriction endonuclease, any endonuclease will suffice. Typically, Type II endonucleases are preferred such as EcoRI, Mse1, Pst1, etc. In certain embodiments a type IIs endonuclease may be used, i.e., an endonuclease of which the recognition sequence is located distant from the restriction site, i.e., such as Acell1, Bbv1, BbvII, Bbs1, Bcd, Bce83I, Bcef1, Bcg1, Bin1, Bsa1, Bsg1, BsmAI, BsmF1, BspMI, Esp3I, Fau1, Fok1, Gsu1, Hga1, MboII, Mme1, MnII, Sap1, SfaNI, TaqJI and Zth11 III, as has been disclosed in WO 2007/114693, page 13, lines 3-11.

Mechanical fragmenting can be done by shearing the cDNA, wherein the severity and duration of shearing determine the amount of fragmenting. One such shearing method is nebulization. A nebulizer is a small plastic device that uses compressed air to atomize liquids. They are easily adapted for shearing DNA, extremely efficient and simple to use (Surzycki, S., (2000), *Basic Methods in Molecular Biology*, NY—Springer Verlag). They are commercially available from different sources (e.g., Invitrogen Corporation).

Again complexity reduction can be optionally performed on this fragmented DNA by size selection. Optionally complexity reduction can be obtained by size selection of the fragments, e.g., by electrophoresis. Additionally, or alternatively, poly-A fragments can be removed by binding to streptavidin coated affinity columns.

In the next step of the method, the cDNA fragments are made blunt ended, a process also indicated as 'polishing'. Insert polishing is used to remove 3 prime overhang nucleotide(s) or fill in 5 prime overhang nucleotides from restriction enzyme generated, PCR-generated DNA fragments or sheared DNA fragments. Kits for polishing are commercially available (e.g., Quick blunt kit, New England Biolabs, Inc.).

In the next step of the method of the invention, the cDNA fragments are provided with adaptors through a ligation reaction. In this reaction two different types of adaptors are ligated to a mixture of cDNA fragments. One adaptor is carrying a biotin label. The other adaptor contains a restriction site for a type II restriction enzyme that cuts outside its recognition sequence. An example of this is SapI that recognises the GCTCTTCNNNN sequence (SEQ ID NO:1). The enzyme cuts in the NNNN sequence leaving an NNN overhang on the 5' end. In this way the complete adaptor sequence containing the restriction recognition sequence can be removed from the fragment. It is important to use an enzyme that is a rare cutter to prevent shortening of the fragments by a more frequent occurrence of recognition sequences in the fragment DNA.

Again, at this stage, optionally the fragments can be selected dependent upon their size by, e.g., electrophoresis.

After ligation of the adaptors to the fragments, the fragments are subjected to nick repair, to fill any gap in the DNA backbone that may have been created by ligation of the adaptors.

Figure 3:
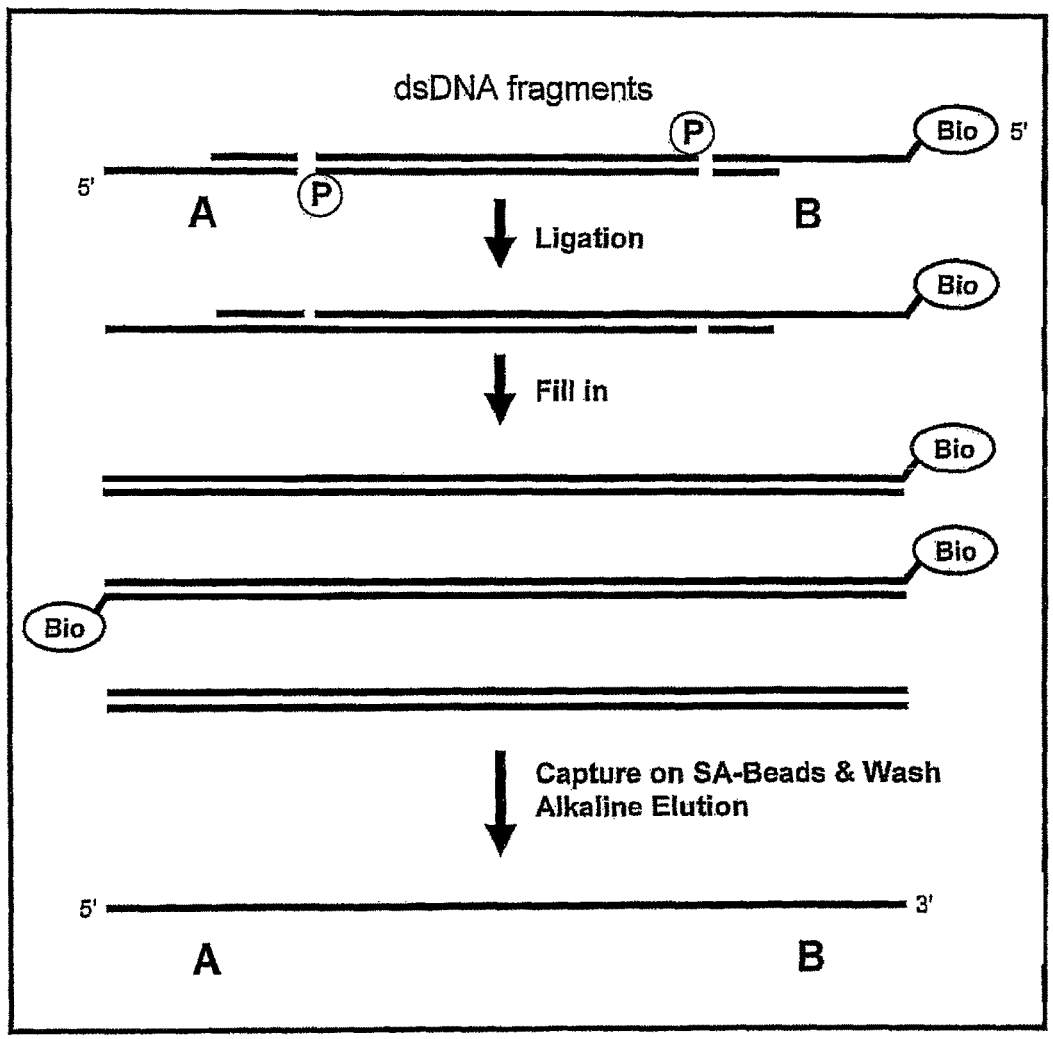
FIG. 3. Non-phosphorylated A and B adaptors are ligated to the ends of phosphorylated, polished, double-stranded genomic DNA fragments. The A and B adaptors differ in both nucleotide sequence and the presence of a 5' biotin tag on the B adaptor. Nicks are present at the 3'-junctions of each of the adaptors and the fragments are filled in by the strand-displacement activity of Bst DNA polymerase. Streptavidin-biotin interactions are used to remove fragments flanked by homozygous adaptor sets (A/A and B/B) and to generate single stranded library templates. Fragments are bound to Streptavidin beads; unbound material (composed of homozygous A/A adaptor sets, which lack biotin) is washed away. The immobilized fragments are then denatured; both strands of the B/B fragments remain immobilized through the biotinylated B adaptor, while A/B fragments are washed free and used in subsequent steps.

Fragments that only contain both adaptors can be selected as described in the Supplementary FIG. 1 of the publication by Margulies, M., et al., in *Nature* (2005) 437:376-380 (FIG. 3). Fragments that contain both adaptors can then be amplified. In this step a PCR amplification reaction is performed with one primer annealing to one of the complementary adaptor sequences in combination with another primer carrying a biotin molecule annealing to the other complementary adaptor sequence. After performing an amplification step using this set of primers, the amplified double stranded DNA fragments are captured on streptavidin affinity beads while other reaction products are removed from the reaction mixture.

In a next step, the bound DNA fragments, having different adaptor sequences at their 5' and 3' termini, are treated with an asymmetric endonuclease cutting the fragment in such a way as to remove a complete adaptor sequence from one end of the fragment, as described earlier, thus providing one fragment terminus that is perfectly complementary to genomic DNA. After this restriction step, free single stranded forms of the fragments are removed by elution from the beads under alkaline conditions, resulting in a set of single stranded nucleic acid fragments bound to streptavidin beads. An alternative method for generating single stranded fragments from double stranded fragments is treatment with lambda exonuclease enzyme. Lambda exonuclease degrades from a double stranded DNA molecule those strands that posses phosphorylated 5' termini, leaving single strands with 5'OH termini intact. Since one of the 5' ends of the fragment is protected by the biotin label that is bound to the streptavidin, treatment with lambda exonuclease also creates single strand DNA fragments bound to the streptavidin beads. These single strand DNA fragments will be used in later steps.

Next to the steps described above, in the second part genomic DNA is isolated from the organism. This organism can be the same as from which the mRNA is isolated (cultured under the same or different conditions) or it can be a different organism (different strain, different species) and it can even be a collection of genomic DNAs (e.g., a BAC clone library). Procedures for isolating genomic DNA are standard in the field and are, e.g., described in Ausubel, et al. (Preparation of genomic DNA from plant tissue. pp. 2.3.1-2.3.7 in Ausubelf, et al., eds. *Current Protocols in Molecular Biology*. John Wiley & Sons, Inc. Budelier. 1993). After isolation, the genomic DNA is fragmented by enzymatic or mechanical fragmentation procedures as described above. If restriction enzyme digestion is used, the resulting fragments are provided with adaptors matching the different restriction site overhangs at the termini of the fragments. The adaptor molecules attached to genomic DNA fragments have sequences that are different from the adaptor molecules attached to cDNA derived fragments of part 1.

If mechanical fragmentation is used, the different adaptors are ligated to the genomic DNA fragments and fragments having different adaptors at the 5' and 3' termini are selected according to the procedure previously described for cDNA fragments (e.g., a polishing step can be applied).

Alternatively, also one single adaptor can be ligated to the genomic fragments. In that case adaptor sequences with panhandles can be used to prevent non-specific amplification in later steps (Jones, D. H., and S C Winistorfer, *PCR Methods Appl*. (1993) 2:197-203).

The fragmented genomic DNA fragments can be optionally size-selected as described above.

To obtain single stranded genomic DNA fragments a melting out step is provided.

After thus providing an appropriate sample of fragmented genomic single stranded DNA, the single stranded cDNA fragments from part 1, carrying a single adaptor molecule with a biotin label which may be optionally bound to streptavidin affinity beads, are mixed in preferentially a molar excess of, for hybridization with the fragmented genomic DNA carrying different adaptor molecules (part 3). After a denaturation step, annealing conditions are applied to allow formation of hybrid double stranded genomic DNA-cDNA molecules.

The hybridization procedure may include a short period of pre-annealing with non-fragmented cDNA (without adaptors) to normalize the hybridization reaction by reducing the effects of higher concentrations of cDNA fragments derived from abundant transcripts. As an optional modification, Cot-1-DNA may be used in a pre-annealing step to reduce possible anomalies caused by sequence repeats in genomic DNA.

In this step the cDNA fragments will anneal to the genomic DNA at places that are homologous or identical to the sampled mRNA.

After extension of the cDNA-genomic DNA hybrid by a polymerase a double-stranded template is made.

The annealed double stranded fragments can now be amplified by a PCR reaction using one primer complementary with the cDNA adaptor and another primer complementary to one of the genomic DNA adaptors. Optionally the annealed material can be separated into two separate fractions to also use the cDNA adaptor and the other primer complementary to the genomic DNA adaptor. The amplification provides PCR fragments that do not only contain copies of the genomic DNA corresponding part of the originally sampled nucleic acid, but also contain non-transcribed sequences, such as regulatory sequences and introns.

After the PCR amplification, fragments of more than 100 basepairs, more preferably more than about 200 basepairs, even more preferably more than about 300 basepairs and most preferably of about 400 basepairs or more are selected through size fractionation. Optionally, these fragments are purified according to meet the requirements for the next part of the method of the invention.

In the next part (part 4) said fragments are sequenced. Sequencing of the amplified adaptor-ligated fragments provides sequence information on at least part of the adaptor-ligated fragment and the 3' flanking genomic sequences. The information contained in the adaptor-derived part contains information about the sample from which the fragment is obtained if adaptors carry sample specific tags, whereas sequence information from the fragment itself (an identifier sequence) provides information about the fragment and allows for identification of the fragment. This sequence information on the fragment is used to identify the fragment with an accuracy that depends on the number of nucleotides that is determined and the number of fragments in the set of amplified adaptor-ligated fragments.

To provide a solution to the problem of sampling variation in transcript frequencies between samples, which affects the accuracy of identifying molecular markers by sequencing contained in a set of multiple fragments, the present inventors have also found that detection of markers via sequencing is preferably performed with sufficient redundancy (depth) to sample all fragments at least once and accompanied by statistical means which address the issue of sampling variation in relation to the accuracy of the genotypes called. In order to increase the accuracy, preferably an amplification step proceeds the sequencing step. After sufficient cycles of amplification, the redundancy of the amplified adaptor-ligated restriction fragments is at least 6, preferably at least 7, more preferably at least 8 and most preferably at least 9. In preferred embodiments thus the sequence of each adaptor-ligated restriction fragment is determined at least 6, preferably at least 7, more preferably at least 8 and most preferably at least 9 fold. In certain embodiments, the redundancy is selected such, assuming a 50/50 overall chance of identifying the locus correctly as homozygous, that the chance of correct identification of the locus is more than 95%, 96%, 97%, 98%, 99%, 99.5%.

The amplification of the adaptor-ligated restriction fragments leads to a set of amplified adaptor-ligated restriction fragments, sometimes referred to as amplicons. The amplicons (or at least part thereof) are subjected to a step that comprises at least the determination of the sequence of the sample specific identifier to determine the origin of the fragment and of part of the sequence of the restriction fragment. In practice this amounts also to the determination of the sections located in between such as the remains of the recognition sequence of the restriction endonuclease. By sequencing the sample specific identifier in combination with part of the fragment located adjacent to the adaptor derived sequence, it is possible to uniquely identify restriction fragments and their 3' flanking genomic sequences. From this information it is possible to restore the genomic genetic information of a complete gene.

The high-throughput sequencing used in the present invention is a method for scientific experimentation especially relevant to the fields of biology and chemistry.

The following description of high-throughput sequencing methods, especially the Illumina-Solexa technologies, has been based on the description given in WO 2007/114693 (applicant: KeyGene B. V., inventors: M. J. T. Van Eijk, R. C. J. Hogers, agent: R. J De Lang of Exter Polak & Charlouis B. V.) and WO 2006/137733 (applicant: KeyGene B. V., inventors: M. J. T. Van Eijk, H. J. A. Van der Poel, agent: R. J De Lang of Exter Polak & Charlouis B. V.); direct citations are provided in italics.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo, et al., *Proc. Natl. Acad. Sci. USA* (2004) 101:5488-5493, and technologies of Helios, Solexa, US Genomics, etcetera, which are herein incorporated by reference.

The technology described allows sequencing of 40 million bases in a single run and is 100 times faster and cheaper than competing technology. The sequencing technology roughly consists of 5 steps: 1) fragmentation of DNA and ligation of specific adaptors to create a library of single-stranded DNA (ssDNA), 2) annealing of ssDNA to beads, emulsification of the beads in water-in-oil microreactors and performing emulsion PCR to amplify the individual ssDNA molecules on beads, 3) selection or enrichment for beads containing amplified ssDNA molecules on their surface, 4) deposition of DNA carrying beads in a PicoTiter™ Plate; and 5) simultaneous sequencing in 100,000 wells by generation of a pyrophosphate light signal. The method will be explained in more detail below.

In this respect the following calculation may be illustrative: The sequencing technology of Illumina Solexa as described herein elsewhere, provides for 40,000,000 reads of about 25 bp each, totaling a staggering 1 billion by in one single run. Assuming a redundancy in sampling of 10 times, 4,000,000 unique fragments can be assessed in one run. Combining 100 samples allows for 40,000 fragments to be sequenced for each sample.

In a preferred embodiment, the sequencing comprises the steps of: (a) annealing adapted fragments to beads, each bead being annealed with a single adapted fragment;

(b) emulsifying the beads in water-in-oil microreactors, each water-in-oil microreactor comprising a single bead;

(c) loading the beads in wells, each well comprising a-single bead; and generating a pyrophosphate signal.

In the first step (a), sequencing adaptors are ligated to fragments within the combination library. Said sequencing adaptor includes at least a "key" region for annealing to a bead, a sequencing primer region and a PCR primer region. Thus, adapted fragments are obtained. In a first step, adapted fragments are annealed to beads, each bead annealing with a single adapted fragment. To the pool of adapted fragments, beads are added in excess as to ensure annealing of one single adapted fragment per bead for the majority of the beads (Poisson distribution). In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments. After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on the World Wide Web at biotagebio.com; pyrosequencing.com/section technology. The technology is further applied in, e.g., WO 03/004690, WO 03/054142, WO 2004/069849, WO 2004/070005, WO 2004/070007, and WO 2005/003375 (all in the name of 454 Life Sciences). In the present invention, the beads are preferably equipped with primer (binding) sequences or parts thereof that are capable of binding the amplicons, as the case may be. In other embodiments, the primers used in the amplification are equipped with sequences, for instance at their 5'-end, that allow binding of the amplicons to the beads in order to allow subsequent emulsion polymerization followed by sequencing. Alternatively the amplicons may be ligated with sequencing adaptors prior to ligation to the beads or the surface. The sequenced amplicons will reveal the identity of the identifier and thus of the presence or absence of the restriction-fragment in the sample.

Illumina-Solexa Technologies

One of the methods for high throughput sequencing is available from Illumina, United Kingdom (located on the World Wide Web at illumina.co.uk) and described inter alia in WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089 and WO2005078130. In essence, the method starts with adaptor-ligated fragments of genomic DNA. The adaptor-ligated DNA is randomly attached to a dense lawn of primers that are attached to a solid surface, typically in a flow cell. The other end of the adaptor ligated fragment hybridizes to a complementary primer on the surface. The primers are extended in the presence of nucleotides and polymerases in a so-called solid-phase bridge amplification to provide double stranded fragments. This solid phase bridge amplification may be a selective amplification.

Denaturation and repetition of the solid-phase bridge amplification results in dense clusters of amplified fragments distributed over the surface. The sequencing is initiated by adding four differently labeled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues.

In the present invention, the adaptor ligated restriction fragments or the amplicons are bound to the surface via the primer binding sequence or the primer sequence. The sequence is determined as outlined, including the identifier sequence and the restriction fragment. Currently available Solexa technology allows for the sequencing of fragments of about 30 base pairs. By smart design of the adaptors and the surface bound primers, the sequencing step reads through the sample identifier and the remains of the recognition sequence of the restriction endonuclease used. For example when an 3 bp sample identifier is used and the remains of the rare cutter EcoRI (GAACCT) are present, an internal sequence of the restriction fragment of 7 bp that can be used to uniquely identify the restriction fragment in the sample.

In a preferred embodiment based on the Illumina-Solexa sequencing technology above, the amplification of the adaptor ligated restriction fragments is performed with a primer that contains at most one selective nucleotide at its 3' end, preferably no selective nucleotides at its 3' end, i.e., the primer is only complementary to the adaptor (a +0 primer).

In alternative embodiments directed to the sequencing methods described herein, the primers used in the amplification may contain specific sections (as alternative to the herein described primer or primer binding sequences) that are used in the subsequent sequencing step to bind the adaptor-capped restriction fragments or amplicons to the surface. These are generally depicted as the key region or the 5'-primer compatible sequence.

In one embodiment of the invention, the nucleic acid sample is digested with at least one restriction enzyme and at least one adaptor is ligated that comprises a recognition sequence for a type II restriction endonuclease. The subsequent digestion of the adaptor-ligated restriction fragment with a type IIs restriction endonuclease yields, as the distance between the recognition and restriction site of a type IIs enzyme is relatively short (up to about 30 nucleotides), a shorter and a longer restriction fragment, to which a IIs restriction site compatible adaptor can be ligated. Typically, the overhang of the IIs-restricted site is unknown such that a set of adaptors may be used that are degenerated in the overhang. After (selective) amplification, the amplicons can be sequenced. The adaptor sequence in this embodiment generally can be described as: 5'-primer binding site-sample identifier sequence-degenerate type IIs cohesive end sequence-3'. The associated PCR primer generally follows: primer sequence-sample identifier sequence-degenerate type IIs cohesive end sequence-selective nucleotides-3'. The primer used to initiate the sequencing-by-synthesis then generally has the structure: 5'-primer binding site-3'. A size selection step may be preferred after digesting with the IIs enzyme to remove the smaller fragments. As in this embodiment the remains of the restriction site are for this type of enzyme typically in the order of 2-4 bp, this results in combination with a 6 bp sample identifier in the sequencing of 15-17 bp of a restriction fragment.

Thus the method of the invention is perfectly suited to identify the regulatory genomic sequences of genes belonging to the transcriptome of a cell or organism, without any initial sequence information or prior genetic knowledge of the cell and/or of the organism from which the cell is derived. Accordingly, the promoter region, leader sequences and other 5' UTR regions, introns and exons, the 3' UTR sequences and terminator of an expressed gene can be identified according to the present method. Since no cloning step is involved, it is also feasible to determine the genomic sequences of genes that cause problems in cloning steps, e.g., genes that are toxic to the host organism, genes that code for regulatory proteins and/or genes that cause otherwise problems in cloning.

Further, it is possible on basis of this information to directly analyze all polymorphisms (including SNPs) associated with the alleles of an expressed gene, whether these polymorphisms occur in the coding sequence or in the non-coding sequence of the gene. Thus, it will be possible to detect aberrations in promoter sequences that cause a regulation of gene expression, it will be possible to detect mutants with polymorphisms in the introns that can cause different splice variants, and so on.

In order to increase a correct interpretation of the sequenced nucleic acid sequences and the differences found therein, automatic annotation can be performed on the sequenced fragments or contigs.

Similarly, the obtained sequence information can be used to compare the sequences with sequences from an EST library. In that way intron sequences or gene internal non-coding sequences, as well as promoter sequences and 3' and 5' UTRs can be identified. The EST library can be taken from the same organism or from a related species.

In a further aspect, the invention relates to kits with which the method of the invention can be performed. Such kits would comprise one or more adaptors and optionally one or more primers complementary to said adaptors, ligase, and/or restriction enzymes that are specific for cutting the adaptors, aside from conventional components for amplification kits per se, like dNTPs, polymerase, etc. Further, the kit should provide instructions for use, wherein an instruction scheme for performing the method of the invention.

Furthermore, the present invention finds application in, amongst others, use of the method for the identification of molecular markers, for genotyping, bulk segregant analysis, genetic mapping, marker-assisted back-crossing, mapping of quantitative trait loci, linkage disequilibrium mapping, and determination of methylation patterns.

EXAMPLE cDNA Procedure
RNA Isolation and cDNA Synthesis

Total RNA was isolated from skin of apple fruit, *Malus*× *domestica*, cultivar Kanzi, following the method of Chang, et al. (1993). Apples were derived from 4 different orchards and picked at 5 different time-points in 2007 from early August until late September. Equal amounts of total RNA from these 20 samples were pooled into one sample and purified with the RNeasy Plus Micro Kit (QIAGEN, Hilden, Germany, 74034) to remove genomic DNA contamination according to manufacturer's instructions.

First-strand cDNA synthesis was performed with 2 µg total RNA as input using the Mint cDNA synthesis kit (Evrogen, Moscow, Russia, SK001) according to manufacturer's instructions. Double-stranded (ds) cDNA synthesis by PCR amplification was performed using the Mint cDNA synthesis kit for an optimal of 18 cycles. The obtained ds cDNA was purified using QIAquick® PCR Purification columns (QIAGEN, 28104) and the concentration was measured spectrophotometrically. The cDNA was analyzed on a 1% agarose gel. The ds cDNA ranged from 200 to 2000 bp.

cDNA Blunting, Phosphorylation, Concatenation and Nebulization

The ds cDNA was blunted and phosphorylated using the Quick Blunting™ Kit (New England Biolabs, Ipswich, Mass., USA, E1201S). 38 µl cDNA (8 µg) was mixed with 5 µl 10× Blunting Buffer, 5 µl 1 mM Deoxynucleotide Solution Mix and 2 µl Blunting Enzyme Mix and incubated at room temperature for 30 minutes, followed by 10 minutes at 70° C.

Subsequently, 48 µl of this cDNA blunting mixture was concatenated by mixing it with 10 µl 10×T4 DNA Ligase Reaction Buffer, 5 µl T4 DNA Ligase (both from New England Biolabs, M0202S, 400,000 U/ml), 25 µl 40% (w/v) polyethyleneglycol 8000 and 12 µl water. The ligation mixture was incubated for 2 hours at room temperature and concatenation was confirmed by agarose gel analysis. The T4 ligase was inactivated by incubation at 65° C. for 10 minutes.

The concatenated cDNA was subjected to shearing by nebulization. The cDNA ligation mixture of 100 µl was mixed with 650 µl nebulization buffer (10 mM Tris-HCl, 1 mM EDTA, 50% glycerol, pH 8.0) and pipetted into a nebulizer (Invitrogen, Paisley, UK, K7025-05). Nebulization was carried out following manufacturer's instructions for 15 minutes at 48 psi using nitrogen gas 5.0 (Praxair, Danbury, Conn., USA). After short centrifugation of the nebulizer, the collected nebulized cDNA was transferred to a microcentrifuge tube and precipitated by addition of 2 µl glycogen (Sigma-Aldrich, St. Louis, Mo., USA, 20 mg/ml, G 1767), 0.1 volume of 3M sodium acetate pH 5.2 and 1 volume of isopropanol, and incubation for 10 minutes at −80° C. The cDNA was pelleted by centrifugation for 15 minutes at 20,800 g, washed with 70% ethanol, dried and dissolved in 50 µl 10 mM Tris-HCl, 1 mM EDTA, pH 8.0.

cDNA Sizing and Blunting

The sheared cDNA was incubated at 65° C. for 10 minutes, gel loading buffer was added and the cDNA was divided over 5 slots of a 2% agarose gel in Tris-acetate (TAE) buffer (Sambrook, et al., 1989). After electrophoresis, cDNA fragments of 100-400 bp were isolated from the gel using the GenElute Gel Extraction kit (Sigma-Aldrich, NA1111). A small sample of the purified cDNA was checked on gel and the concentration was found to be low. Therefore, the procedures above of cDNA blunting, phosphorylating, concatenation, nebulization and gel purification was repeated several times with a total of 24 µg ds cDNA obtained with the Mint cDNA synthesis kit. The cDNA fragments of 100-400 bp were concentrated by ethanol precipitation and dissolved in 19 µl molecular biology-grade water.

The frayed ends of the sheared cDNA were blunted and phosphorylated by mixing with 2.5 µl 10× Blunting Buffer, 2.5 µl 1 mM Deoxynucleotide Solution Mix and 1 µl Blunting Enzyme Mix from the Quick Blunting™ Kit (New England Biolabs, E1201S) and incubation at room temperature for 30 minutes, followed by 10 minutes at 70° C. Subsequently, the cDNA was purified using the MinElute® PCR Purification Kit (QIAGEN, 28004).

Adaptor Ligation and Nick-Repair

Adaptor ELTD-AdC was prepared by annealing of the partially complementary oligonucleotides ELTD-Primer-C (5'-AGTCCGTCGCATCGCTCTTC-3') (SEQ ID NO:2) and ELTD-AdC2 (5'-GAAGAGCGATGCGACG-3') (SEQ ID NO:3). This adaptor is blunt on one side and has a 4 nt (AGTC) 5'-overhang on the other side to achieve directionality of ligation to the cDNA and to prevent ligation of multiple adaptors to the cDNA. The ELTD-AdC adaptor also contains the rare cutting SapI restriction site (SEQ ID NO:1):

GCTCTTCN/NNN

CGAGAAGNNNN/

This restriction site enables removal of ELTD-AdC from the cDNA during a later step in the protocol. Adaptor ELTD-AdD was prepared by annealing of the partially complementary oligonucleotides ELTD-Primer-D (5'-Biotin-TEG-AGTGGGTGTCCTGGGTC AAC-3') (SEQ ID NO:4) and ELTD-AdD2 (5'-GTTGACCCAGGACACC-3') (SEQ ID NO:5). This adaptor also has a 4 nt (AGTG) 5'-overhang on one side, which is labeled with biotin via a tetra-ethyleneglycol (TEG) spacer arm. The biotin label will enable immobilization of the cDNA to streptavidin-coated beads during later steps in the protocol. All oligonucleotides were ordered HPLC-purified from Sigma-Aldrich and dissolved in 1 mM Tris-HCl, 0.1 mM EDTA, pH 8.0. The adaptors were prepared by mixing 50 µl of each of the appropriate oligonucleotide (400 µM) with 100 µl of 2× annealing buffer (20 mM Tris-HCl, 100 mM NaCl, 2 mM EDTA, pH 7.6), incubating the mixture for 5 minutes at 95° C. in a thermoblock (Thermomixer Compact, Eppendorf, Hamburg, Germany), then switching off the thermoblock allowing the samples inside to slowly cool down to less than 30° C. (taking 3 hours). This yielded the double-stranded adaptors ELTD-AdC and ELTD-AdD at 100 µM concentrations.

Both adaptors were ligated to the cDNA in the following reaction: 9.2 µl cDNA from the MinElute purification column, 1.25 µl water, 0.4 µl adaptor ELTD-AdC (100 µM), 0.4 µl adaptor ELTD-AdD (100 µM), 12.5 µl 2× Quick Ligation Reaction Buffer and 1.25 µl Quick T4 DNA Ligase (Quick Ligation™ Kit, New England Biolabs, M2200S). The ligation mixture was incubated at 25° C. for 20 minutes and purified using the GenElute PCR Clean-Up Kit (Sigma-Aldrich, NA1020).

The adaptor-ligated cDNA was nick-repaired in the following reaction: 47 µl cDNA from the GenElute purification column, 8 µl 10× ThermoPol Reaction Buffer (New England Biolabs), 8 µl 1 mg/ml BSA, 2 µl 10 mM dNTPs, 1 µl 8 U/µl Bst DNA Polymerase, Large Fragment (New England Biolabs, M0275) and 14 µl water. The nick-repair reaction was incubated for 30 minutes at 65° C. and purified using a QIAquick PCR purification column yielding 50 µl 100-400 bp adaptor-ligated cDNA.

Amplification of Adaptor-Ligated cDNA

The cDNA was amplified with a high-fidelity DNA polymerase in a PCR reaction containing: 10 µl cDNA from the QIAquick PCR purification column, 10 µl 5× Phusion™ HF buffer, 1 µl 10 mM dNTPs, 2.5 µl 10 µM ELTD-Primer-C, 2.5 µl 10 µM ELTD-Primer-D, 0.5 µl 2 U/µl Phusion Hot Start DNA Polymerase (Finnzymes, Espoo, Finland, F-540) and 23.5 µl water. First, a test was carried out to determine the optimal number of PCR cycles for cDNA amplification. The reaction mixture was placed in a thermal cycler, denatured at 98° C. for 30 sec and subsequently subjected to 5 cycles of denaturation-annealing-elongation: 5 sec at 98° C., 10 sec at 60° C., 15 sec at 72° C. After this, 5 µl was removed from the reaction mixture and kept on ice (sample after 5 cycles). The remaining reaction mixture was subjected to three more PCR cycles as above and 5 µl was removed and kept on ice (sample after 8 cycles). The above was repeated 5 more times until a total of 23 cycles had been reached. The 5 µl samples of 5, 8, 11, 14, 17, 20 and 23 cycles were analyzed on a 1.5% agarose gel. The optimum number of cycles was determined to be 17 cycles, after that a plateau was reached as more cycles led to the appearance of a smear above the expected size of the cDNA. To make more cDNA, two PCR reaction mixtures each with 10 µl cDNA were prepared as described above. The reaction mixtures were placed in a thermal cycler, denatured at 98° C. for 30 sec and subsequently subjected to 17 cycles of denaturation-annealing-elongation: 5 sec at 98° C., 10 sec at 60° C., 15 sec at 72° C. A final extension step of 5 min at 72° C. followed. The amplified cDNA was purified using a QIAquick PCR purification column, followed by a GenElute PCR Clean-Up column (Sigma-Aldrich) to remove primers and possible primer-dimers.

Isolation of Single-Stranded CD-Adapted cDNA

Next, cDNA obtained in the previous step was enriched for molecules carrying ELTD-Ad-C on one end and ELTD-Ad-D on the other end by binding to streptavidin-coated beads, washing and alkaline elution. cDNA molecules carrying ELTD-Ad-C on both ends (from now on called CC molecules) cannot bind to streptavidin and are washed away from the beads. cDNA molecules carrying ELTD-Ad-D on both ends (from now on called DD molecules) will stay bound to the beads during alkaline elution, since both strands are biotinylated. cDNA molecules carrying ELTD-Ad-C on one end and ELTD-Ad-D on the other end (from now on called CD molecules) will stay bound to the beads with one biotinylated strand, the other non-biotinylated strand will be eluted by treatment with NaOH.

Streptavidin-coated paramagnetic Dynabeads® M-270 (Invitrogen, 653.05) were thoroughly resuspended and 50 µl (corresponding to 0.5 mg) beads was transferred to a siliconized microcentrifuge tube (Sigma-Aldrich, T4816). Beads were washed three times with 100 µl 1×B&W buffer (5 mM Tris-HCl, 0.5 mM EDTA, 1 M NaCl, pH 7.5) using a Dynal magnetic stand (MPC®-E-1, Invitrogen) for separation of the beads following manufacturer's instructions. Beads were resuspended in 100 µl 2×B&W buffer containing 0.02% Tween-20 to decrease a specific binding. Next, 45 µl of PCR-amplified and purified cDNA mixed with 55 µl of water was added to the bead suspension. cDNA was allowed to bind for 15 min at room temperature with gentle rotation of the tube. The tube was placed in the magnetic stand to separate the beads from the supernatant, which was transferred to a fresh tube. This fraction is called AB (after binding) and contains cDNA which was not bound to the beads. Subsequently, the bead pellet was washed as follows: once with 200 µl 2×B&W buffer containing 0.02% Tween-20, once with 500 µl 2×B&W buffer containing 0.02% Tween-20 and twice with 500 µl water. After resuspension of the beads in water for the second time, beads were transferred to a fresh siliconized tube before transfer to the magnet. Finally, the beads were resuspended in 250 µl freshly prepared 0.1 M NaOH and the tube was gently rotated for 2-3 minutes. The supernatant represents the first elution. The beads were again resuspended in 250 µl 0.1 M NaOH and gently rotated for 2-3 minutes, this supernatant represents the second elution. Elutions were each mixed with 1250 µl PBI buffer (QIAquick PCR purification kit) and 7.2 µl 20% acetic acid and purified over QIAquick PCR purification columns. Also, the AB fraction was purified over a QIAquick PCR purification column. Remaining beads were washed once with 200 µl water, once with 200 µl 10 mM Tris-HCl, 1 mM EDTA, pH 8.0, once again with 200 µl water and finally resuspended in 50 µl water and stored at 4° C.

Five microliter of the AB fraction and both alkaline elutions were checked on a 1.5% agarose gel. cDNA was found in the AB fraction and the first alkaline elution, but not in the second alkaline elution, which was discarded. Control PCR reactions were carried out on 1 µl of the AB fraction, first alkaline elution and the beads (50 µl total volume each). Each was mixed with 12.5 µl REDTaq® ReadyMix™ (Sigma-Aldrich, R2523), 1 µl 10 µM ELTD-Primer-C or 1 µl 10 µM ELTD-Primer-D or [1 µl 10 µM ELTD-Primer-C and 1 µl 10 µM ELTD-Primer-D] and water to a total volume of 25 µl. PCR conditions were: 1 min@94° C., (30 sec@94° C., 30 sec@50° C., 30 sec@72° C.) for 6, 9, 12 and 15 cycles, 5 min@72° C. Of each reaction 5 µl was loaded on a 1.5% agarose gel. The results showed that there were more CC than DD and CD-molecules in the AB fraction as expected, because CC molecules cannot bind to the beads. In the alkaline elution and the bead fraction the occurrence was: CC<DD<CD. The conclusion was that there was enrichment for CD molecules in the alkaline eluate as expected, but that CC and especially DD molecules were also still present, probably due to aspecific binding of CC and incomplete binding of DD molecules to the beads. The alkaline elution (QIAquick-purified) is called the single-stranded CD-enriched cDNA.

Amplification of the CD-Enriched cDNA

After testing the optimal PCR conditions, the single-stranded CD-enriched cDNA was amplified as follows. Sixteen PCR reactions were set up each containing: 0.5 µl of the QIAquick column-purified first alkaline elution of the Dynabeads described above, 10 µl 5× Phusion™ HF buffer, 1 µl 10 mM dNTPs, 2.5 µl 10 µM ELTD-Primer-C, 2.5 µl 10 µM ELTD-Primer-D, 0.5 µl 2 U/µl Phusion Hot Start DNA Polymerase (Finnzymes, F-540) and 33 µl water. The reaction mixtures were placed in a thermal cycler, denatured at 98° C. for 30 sec and subsequently subjected to 11 cycles of denaturation-annealing-elongation: 5 sec at 98° C., 10 sec at 60° C., 15 sec at 72° C. A final extension step of 5 min at 72° C. followed. The amplified cDNA was purified using three parallel QIAquick PCR purification columns. The purified cDNA was analyzed on a 1.2% agarose gel and the concentration was measured spectrophotometrically. A total of 27.5 µg of double-stranded CD-enriched cDNA was obtained.

Binding of the CD-Enriched cDNA to Dynabeads

Five microgram of the double-stranded CD-enriched cDNA from the previous step was used to bind to Dynabeads M-270. The procedure is described above under 'Isolation of single-stranded CD-adapted cDNA' with the following modifications. An amount of 27.32 µl corresponding to 5 µg of the CD-enriched cDNA was mixed with water to a volume of 100 µl in total, and this mixture was added to the beads in 100 µl 2×B&W buffer containing 0.02% Tween-20. After binding of the cDNA and washing with 2×B&W buffer containing 0.02% Tween-20 and washing with water, the beads were washed 2 times with 200 µl 1× NEBuffer 4 (New England Biolabs). Finally, the beads with the bound cDNA were resuspended in 100 µl 1× NEBuffer 4 and transferred to a new siliconized microcentrifuge tube.

Digestion of the CD-Enriched cDNA-Bead Preparation with SapI

The CD-enriched cDNA on the beads was digested with SapI to remove adaptor ELTD-AdC from the cDNA molecules, while the cDNA remained attached to the beads via biotinylated adaptor ELTD-AdD. Five microliters of Sap I (2 U/µl, New England Biolabs, R0569) was added to the cDNA-bead suspension and incubated for 1.5 hour at 37° C. The beads were vortexed at 1400 rpm every 10 minutes to keep them in suspension during this step. Next, the beads were placed in the magnetic stand for 1 min to separate the beads, the supernatant was discarded and the beads were washed two times with 500 µl 2×B&W buffer containing 0.02% Tween-20 and two times with 500 µl water.

Alkaline Elution to Prepare the Single-Stranded CD-Enriched cDNA-Bead Library

The bead pellet was resuspended in 250 µl 0.1 M NaOH (freshly prepared) and the tube was gently rotated for 2-3 minutes. The tube was put into the magnetic stand for 1 min and the supernatant (=alkaline eluate) was transferred to a fresh tube. The alkaline eluate was mixed with 1250 µl PBI buffer (QIAquick PCR purification kit) and 7.2 µl 20% acetic acid and purified over a QIAquick PCR purification column. The remaining beads were washed once with 200 µl water, once with 200 µl 10 mM Tris-HCl, 1 mM EDTA, pH 8.0, once again with 200 µl water and finally resuspended in 50 µl water and stored at 4° C. This is the single-stranded CD-enriched cDNA-bead library, ready for hybridization with genomic DNA.

The purified alkaline eluate was analyzed on a 1.2% agarose gel together with the after binding fraction from 'Binding of the CD-enriched cDNA to Dynabeads' and a dilution series of double-stranded cDNA of known concentration from 'Amplification of adaptor-ligated cDNA'. Approximately 2 µg of the cDNA was found in the AB fraction and was not bound to the Dynabeads. The alkaline eluate showed a smear of the expected size. The concentration of the alkaline eluate was measured spectrophotometrically and it was found that 410 ng of single-stranded cDNA had been eluted from the beads. In theory, an equal amount of the complementary cDNA strands should be in the single-stranded CD-enriched cDNA-bead library, corresponding to approximately 4 pmol assuming an average size of 300 nt.

Genomic DNA

Isolation of Genomic DNA

Genomic DNA (gDNA) was isolated from Kanzi leaves following the protocol of Kobayashi, et al. (1998). After RNase treatment according to Kobayashi, et al. (1998), the gDNA was precipitated with high-salt to remove impurities by addition of two-third volume 5M NaCl and two volumes ethanol (p.a.), followed by centrifugation for 15 minutes at 20,000 g, washing the pellet with 70% ethanol, drying and dissolving the pellet in 10 mM Tris-HCl, 1 mM EDTA, pH 8.0.

Restriction Enzyme Digestion of the gDNA

The gDNA was fragmented by restriction enzyme digestion to create non-overlapping fragments. Overlapping fragments may interfere with the hybridization step later in the protocol, leading to networks of hybridizing fragments. Restriction digests were chosen which yielded mostly 1-3 kb fragments. The gDNA was digested with HindIII/BstYI and with EcoRI/BstYI to create two sets of different fragments. Twenty micrograms of gDNA was digested by addition of 10 µl NEBuffer 2, 3 µl EcoRI (New England Biolabs, 20 U/µl, R0101) or 1 µl HindIII (New England Biolabs, 100 U/µl, R0104) and water until a total volume of 100 µl, followed by incubation at 37° C. for 1 hour. Subsequently, 6 µl BstYI (New England Biolabs, 10 U/µl, R0523) was added to each tube, followed by incubation at 60° C. for 1 hour. The digested DNA's were each loaded in 4 lanes of a 1% agarose gel and separated. Fragments between 1 and 3 kb were cut from gel and purified using the GenElute Gel Extraction Kit (Sigma-Aldrich, NA1111). The above procedure was repeated one time to generate sufficient DNA fragments. The EcoRI/BstYI (EB) and HindIII/BstYI (HB) genomic fragments were ligated to adaptors ELTD-AdE-Eco, ELTD-AdE-Hind and ELTD-AdF-Bst.

Adaptor Ligation to the gDNA

Adaptor ELTD-AdE-Eco was prepared by annealing of the partially complementary oligonucleotides ELTD-AdE-Eco1 (5'-CTTGTAGGGCACGGGTCGAGAG-3') (SEQ ID NO:6) and ELTD-AdE-Eco2 (5'-AATTCTCTCGACCCGTGCCCTA-3') (SEQ ID NO:7). This adaptor has a 5'-AATT overhang on one side, which is compatible to the EcoRI-overhang of the gDNA fragments and a 5'-CTTG overhang on the other side. These overhangs achieve directionality of ligation to the gDNA and prevent ligation of multiple adaptors to the gDNA. Adaptor ELTD-AdE-Hind was prepared by annealing of the partially complementary oligonucleotides ELTD-AdE-Hind1 (5'-CTTGTAGG GCACGGGTCGGAGA-3') (SEQ ID NO:8) and ELTD-AdE-Hind2 (5'-AGCTTCTCCGACCCGTGCCCTA-3') (SEQ ID NO:9). Analogous to ELTD-AdE-Eco, the ELTD-AdE-Hind adaptor has a HindIII-compatible 5'-AGCT overhang on one side and a 5'-CTTG overhang on the other side. Adaptor ELTD-AdF-Bst was prepared by annealing of the partially complementary oligonucleotides ELTD-AdF-Bst1 (5'-GAATGGCTGGGAGAGTGCTGAG-3') (SEQ ID NO:10) and ELTD-AdF-Bst2 (5'-GATCCTCAGCACTC TCCCAGCC-3') (SEQ ID NO:11). Analogous to ELTD-AdE-Eco, the ELTD-AdF-Bst adaptor has a BstYI-compatible 5'-GATC overhang on one side and a 5'-GAAT overhang on the other side. All oligonucleotides were ordered HPLC-purified from Sigma-Aldrich and dissolved in 1 mM Tris-HCl, 0.1 mM EDTA, pH 8.0.

The adaptors were prepared by mixing 15 µl of each of the appropriate oligonucleotide (800 µM) with 60 µl of 2× annealing buffer (20 mM Tris-HCl, 100 mM NaCl, 2 mM EDTA, pH 7.6) and 30 µl water and incubating the mixture for 5 minutes at 95° C. in a thermoblock, then switching off the thermoblock allowing the samples inside to slowly cool down to less than 30° C. (taking 3 hours). This yielded the double-stranded adaptors ELTD-AdE-Eco, ELTD-AdE-Hind and ELTD-AdF-Bst at 100 µM concentrations.

Adaptors ELTD-AdE-Eco and ELTD-AdF-Bst were ligated to the EcoRI/BstYI (EB) 1-3 kb gDNA fragments in the following reaction: 1.3 µg EB fragments, 0.4 µl adaptor ELTD-AdE-Eco (100 µM), 0.4 µl adaptor ELTD-AdF-Bst (100 µM), 40 µl 2× Quick Ligation Reaction Buffer, 4 µl Quick T4 DNA Ligase (Quick Ligation™ Kit, New England Biolabs, M2200S) and water to a total volume of 80 µl. Adaptors ELTD-AdE-Hind and ELTD-AdF-Bst were ligated to the HindIII/BstYI (HB) 1-3 kb gDNA fragments in the following reaction: 1.0 µg HB fragments, 0.4 µl adaptor ELTD-AdE-Hind (100 µM), 0.4 µl adaptor ELTD-AdF-Bst (100 µM), 40 µl 2× Quick Ligation Reaction Buffer, 4 µl Quick T4 DNA Ligase (Quick Ligation™ Kit, New England Biolabs, M2200S) and water to a total volume of 80 µl. The ligation mixtures were incubated at 25° C. for 20 minutes and purified using the GenElute PCR Clean-Up Kit (Sigma-Aldrich, NA1020).

Nick-Repair and Purification of EB and HB gDNA

The adaptor-ligated gDNA's were nick-repaired in the following reaction: 40 µl gDNA from the GenElute purification column, 8 µl 10× ThermoPol Reaction Buffer, 8 µl 1 mg/ml BSA, 2 µl 10 mM dNTPs, 3 µl 8 U/µl Bst DNA Polymerase, Large Fragment (New England Biolabs, M0275) and 19 µl water. The nick-repair reaction was incubated for 30 minutes at 65° C. and purified using the GenElute PCR Clean-Up Kit (Sigma-Aldrich, NA1020). This yielded 50 µl adaptor-ligated gDNA of 0.02 µg/µl (EB) and 0.014 µg/µl (HB), ready for hybridization with the single-stranded CD-enriched cDNA-bead library.

The adaptor-ligation step was checked by PCR. One nanogram of the adaptor-ligated and nick-repaired EB preparation was used as template in PCR reactions using either primer ELTD-AdE-Eco1 or ELTD-AdF-Bst1 or a combination of both (E, F, EF respectively). Analogously, the adaptor-ligated HB preparation was used as template in PCR reactions using either primer ELTD-AdE-Hind1 or ELTD-AdF-Bst1 or a combination of both (E, F, EF respectively). For EB and HB, the PCR reactions gave a smear in the region of 1-3 kb as expected.

Hybridization and Amplification of Selected Genomic DNA Fragments

Hybridization of cDNA-Bead Library with gDNA Fragments

The hybridization conditions were tested first on firefly luciferase (Luc) gene fragments. Briefly, a single-stranded 200 nt Luc fragment (Luc200) with ELTD-AdC and ELTD-AdD was bound to Dynabeads M-270 via the biotin label of ELTD-AdD. This Luc-bead preparation was hybridized with a 1600 nt Luc fragment ligated with ELTD-AdE and -AdF mixed with an aspecific 1400 nt control DNA fragment. After hybridization and washing, fragments bound to the Luc200 probe were eluted by alkaline treatment and amplified by PCR. It was found that the 1600 nt Luc fragment was eluted at much higher concentration than the aspecific, non-hybridizing control fragment. There was a 24 cycle difference between the appearance of these fragments during PCR ($2^{24}=1.7 \times 10^7$ fold enrichment of Luc1600 assuming 100% PCR efficiency). The same hybridization and washing conditions were used for the cDNA-bead library and gDNA.

The EB and HB gDNA preparations described above, were denatured by heating. First, 13 µl of EB and 12 µl of HB were reduced in a centrifugal vacuum concentrator to 5 µl. The amount of EB corresponds to 0.26 µg or approximately 0.2 pmol of on average 2 kb fragments. The amount of HB corresponds to 0.17 µg or approximately 0.13 pmol of on average 2 kb fragments. The samples were then denatured in a thermal block for 5 min at 95° C. and directly placed on ice.

The single-stranded CD-enriched cDNA-bead library described above was divided over two siliconized tubes (25 µl beads each). The beads were washed three times with 200 µl 6×SSC/0.1% SDS (pre-warmed at 60° C.) and then resuspended in 100 µl 6×SSC/0.1% SDS and kept at 60° C. To one tube the EB gDNA was added, to the other tube the HB gDNA was added. The tubes were incubated for 4 hours at 60° C. with gentle rotation. The beads were washed two times quickly with 500 µl pre-warmed 6×SSC/0.1% SDS (60° C.), three times 15 min with 500 µl 6×SSC/0.1% SDS at 60° C. with rotation, two times 5 min with 500 µl 6×SSC at room temperature with rotation and once quickly with 500 µl water.

Elongation of Hybrids and PCR Amplification of Selected gDNA Fragments

The formed cDNA/gDNA hybrids on the beads were used for elongation of the 3' cDNA ends using hybridized gDNA as template. After the final water wash step, the beads were directly resuspended in a mixture of 77 µl water and 20 µl 5× Phusion™ HF buffer and transferred to a new siliconized tube. Next were added: 2 µl 10 mM dNTPs and 1 µl 2 U/µl Phusion Hot Start DNA Polymerase (Finnzymes, F-540). Elongation was at 72° C. for 2 min. The beads were kept overnight at 0° C.

The beads were used for PCR amplification with different primer combinations. The beads hybridized with EB gDNA were amplified with the following primer sets:
1) ELTD-AdE-Eco1 and ELTD-AdF-Bst1
2) ELTD-AdE-Eco1
3) ELTD-AdF-Bst1.

The beads hybridized with HB gDNA were amplified with the following primer sets:
4) ELTD-AdE-Hind3 and ELTD-AdF-Bst1
5) ELTD-AdE-Hind3
6) ELTD-AdF-Bst1.

ELTD-Primer E-Hind3 has the following sequence: 5'-GTAGGGCACGGGTCGGA GAAGC-3' (SEQ ID NO:12). It is identical to most part of ELTD-AdE-Hind1 and contains 3 extra nt at the 3'end (AGC) to fit on the HindIII site between the ligated adaptor and the gDNA and to confer stronger 3' end binding to the target during annealing.

The PCR reactions included 1 µl of EB or HB beads, 10 µl 5× Phusion™ HF buffer, 1 µl 10 mM dNTPs, 2.5 µl of each primer (10 µM), 0.5 µl 2 U/µl Phusion Hot Start DNA Polymerase (Finnzymes, F-540) and water to a final volume of 50 µl. To determine the optimal cycle number, the reaction mixtures were divided over five 0.2 ml PCR tubes (10 µl each), overlayed with mineral oil, placed in a thermal cycler, denatured at 98° C. for 30 sec and subsequently subjected to 11, 14, 17, 20 and 23 cycles of denaturation-annealing-elongation: 5 sec at 98° C., 10 sec at 60° C., 2 min at 72° C. A final extension step of 5 min at 72° C. followed. Of each reaction, 2.5 µl was analyzed on a 1.2% agarose gel.

In the PCR reactions with ELTD-AdE and/or ELTD-AdF primers, smears were found of fragments ranging from 1-3 kb as expected for gDNA fragments. The combination of both primers gave PCR products for EB and HB samples already at 17 cycles. With ELTD-AdE alone, products were found after 23 cycles, whereas the same intensity of products was found with ELTD-AdF primers after 20 cycles. This is due to the presence of more BstYI-restriction sites (recognition site: RGATCY) in the genome than EcoRI- or HindIII-sites (GAATTC or AAGCTT).

Amplification of Hybrid-Selected gDNA for High-Throughput Sequencing

The PCR reaction with HB gDNA in combination with primers ELTD-AdE-Hind3 and ELTD-AdF-Bst1 and 20 cycles gave the best result: a homogeneous smear ranging from 1-3 kb. The following PCR reaction mixture was prepared twenty-fold to raise sufficient DNA for high-throughput sequencing: 1 µl of HB beads, 10 µl 5× Phusion™ HF buffer, 1 µl 10 mM dNTPs, 2.5 µl ELTD-AdE-Hind3 (10 µM), 2.5 µl ELTD-AdF-Bst1 (10 µM), 0.5 µl 2 U/µl Phusion Hot Start DNA Polymerase and water to a final volume of 50 µl. The reaction mixture was placed in a thermal cycler, denatured at 98° C. for 30 sec and subsequently subjected to 20 cycles of denaturation-annealing-elongation: 5 sec at 98° C., 10 sec at 60° C., 2 min at 72° C. A final extension step of 5 min at 72° C. followed. This so-called hybrid-selected and amplified HB gDNA was purified using two parallel QIAquick PCR purification columns. The yield, which was measured spectrophotometrically, was 14.8 µg. Part of the hybrid-selected HB gDNA was subjected to high-throughput sequencing. Another part was used for cloning and Sanger sequencing.

Amplification of cDNA for High-Throughput Sequencing

To raise sufficient CD-enriched cDNA for high-throughput sequencing, the following PCR reaction mixture was prepared twenty-fold: 0.5 µl of the QIAquick column-purified first alkaline elution of the Dynabeads described under 'Isolation of single-stranded CD-adapted cDNA', 10 µl 5× Phusion™ HF buffer, 1 µl 10 mM dNTPs, 2.5 µl 10 µM ELTD-Primer-C, 2.5 µl 10 µM ELTD-Primer-D-NB, 0.5 µl 2 U/µl Phusion Hot Start DNA Polymerase (Finnzymes, F-540) and 33 µl water. ELTD-Primer D-NB has the same sequence as ELTD-Primer D, but does not contain a biotin label at the 5' end. The reaction mixtures were placed in a thermal cycler, denatured at 98° C. for 30 sec and subsequently subjected to 11 cycles of denaturation-annealing-elongation: 5 sec at 98° C., 10 sec at 60° C., 15 sec at 72° C. A final extension step of 5 min at 72° C. followed. The amplified cDNA was purified using four parallel QIAquick PCR purification columns. The purified cDNA was analyzed on a 1.2% agarose gel and the concentration was measured spectrophotometrically. A total of 29 µg of double-stranded CD-enriched cDNA was obtained. The cDNA was subjected to high-throughput sequencing.

Sequence Analysis of Captured Genomic DNA Molecules.

After capturing genomic DNA with cDNA beads, the beads with cDNA-gDNA hybrids were used for PCR amplification using the genomic DNA specific primer set ELTD-AdE-Hind3 and ELTD-AdF-Bst1. One part of the genomic DNA was cloned and 800 clones were submitted to Sanger sequencing (mean read length 781 bp). Another part of the genomic DNA was subjected to a high-throughput sequencing technology producing sequence reads having a mean length of 337 bp.

Both sequence datasets consisting of 800 individual Sanger sequences and 1370 high throughput sequence reads were analyzed in detail and compared with all available apple ESTs in a public data bank (NCBI, 262.411 entries on Mar. 9, 2009). The program BLASTN (Altschul, S. F., et al., NAR (1997) 25:3389-3402) was used for global alignment of the genomic DNA sequences with the apple EST sequences.

From 800 Sanger sequences 488 showed significant similarity (e value $10^{-10}$) with sequences from the apple EST collection in the public database and from the random set of 1370 genomic DNA sequences, 765 exhibited significant similarity (e value $10^{-10}$) showing that specific capturing of cDNA-related genomic DNA was successful. In addition, local alignment of these genomic DNA sequences revealed that these sequences frequently extend from the 5' or 3' cDNA boundaries or intron regions, showing that the technique enables identification of non-coding areas. If one takes into account that fragments have only been sequenced from one side, that the size of fragments varies between 1 Kb and 3 Kb and that more than 50% of the sequences have identifiable similarity with EST sequences, it seems obvious that a much higher percentage of sequences matching would have been found if fragments would have been sequenced completely and built into contigs before alignment with public EST sequence data.

Since the size of the Apple genome is around 750 Mb and the number of genes in a plant genome is around 30000 with an average length of 1500 bp yielding 45 Mb of coding sequences on the genome, this means that by random sequencing only 6 percent of the genomic fragments could be annotated, whereas with the described method we find over 50 percent annotation.

Three cases of genomic DNA fragments spanning EST boundaries are described from the above example.

Description Three Cases for Example.

Figure 4:
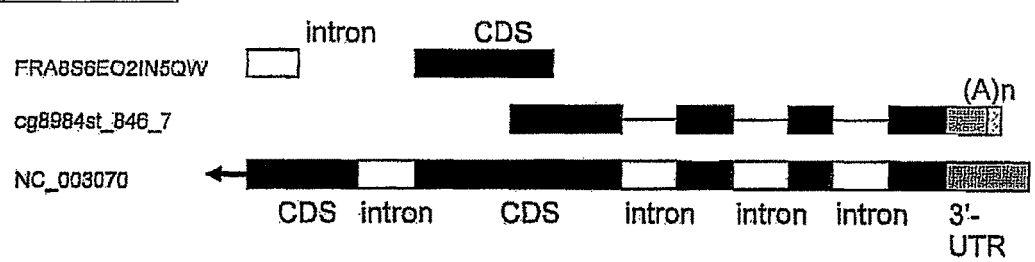
FIG. 4 ELGD schemes cases 1 and 2 and 3. Panel A. Case 1. Schematic representation of the alignment of apple genomic sequence FRA8S6E02IN5QW (SEQ ID NO:18), apple EST contig cg8984st_846_7 (SEQ ID NO:17), and *Arabidopsis thaliana* gene AT1G70160 (SEQ ID NO:16) (not drawn to scale). Only the relevant 3'-part of AT1G70160 is shown. Introns are represented as white boxes in FRA8S6E02IN5QW and AT1G70160. Spliced introns are shown as thin lines in cg8984st_846_7. The protein coding sequences (CDS) are shown in black. The 3'-untranslated regions are shown in grey. The polyA-tail in the cDNA sequence is indicated with (A)n. Panel B. Case 2. Schematic representation of the alignment of apple genomic sequence FRA8SE02HOH39 (SEQ ID NO:19) and apple EST contig cg12357st_1428_21 (SEQ ID NO:22) (not drawn to scale). The protein coding sequence (CDS) is shown in black. The 5'- and 3'-untranslated regions are shown in grey. The polyA-tail in the cDNA sequence is indicated with (A)n. Panel C. Case 3. Schematic representation of the alignment of apple genomic sequence 02-H03 (SEQ ID NO:20) and apple EST 91044590 (SEQ ID NO:21) (not drawn to scale). The protein coding sequence (CDS) is shown in black. The 5'- and 3'-untranslated regions are shown in grey. The non-transcribed promoter region in the genomic sequence is shown in white.
Figure 4:
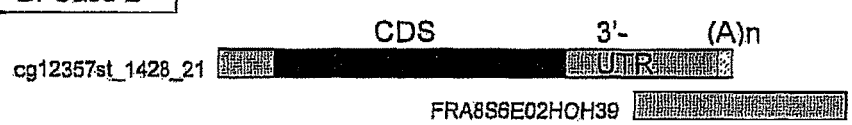
Figure 4:
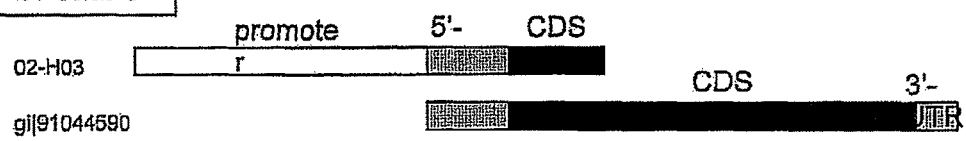

Three cases of apple genomic sequences which were found with the method of the invention are shown in FIG. 4 and the sequence alignments below.

Case 1.

Apple genomic sequence FRA8S6E02IN5QW (sequence, see below) showed 98.9% identity with part of apple contig cg8984st_846_7, built from 7 EST sequences (GenBank Acc: CO899363, CO419003, CO052855, CO752637, CO901846, CN927506 and CO066317).

The best BLASTX (Altschul, S. F., et al., NAR (1997) 25:3389-3402) hit with contig cg8984st_846_7 of *Arabidopsis thaliana* was gene AT1G70160 (genome locus tag, The *Arabidopsis* Information Resource, located on the World Wide Web at *arabidopsis*.org) with e-value 2 $e^{-104}$. Alignment of the three sequences showed that FRA8S6E02IN5QW contains part of the protein coding sequence (CDS) of a protein with unknown function, which partially overlaps with contig cg8984st_846_7. This is shown schematically in FIG. 4, panel A and the sequence alignment of relevant parts of the sequences are shown below. The protein coding sequence of FRA8S6E02IN5QW is also 77.8% identical with AT1G70160, but is interrupted at the 5'-end of the sequence by an intron at the same position as an intron in AT1G70160 (FIG. 4, panel A and sequence alignment). The identity between FRA8S6E02IN5QW and AT1G70160 in this region is low, 37.6%. In AT1G70160 the intron is smaller than in apple (the 5'-boundary of this intron is indicated in bold face in the sequence alignment). In FRA8S6E02IN5QW, there are stop codons in all three reading frames of the intron sequence and BLAST searches indicate that the CDS of FRA8S6E02IN5QW is homologous to similar proteins of other plant species, but that homology is lost in the intron region. This indicates that FRA8S6E02IN5QW is indeed a genomic sequence, containing an interrupting intron sequence. Also here the much lower conservation of intron sequences indicates that intron sequences contain more SNP's than exon sequences.

Case 2.

Apple genomic clone FRA8SE02HOH39 (sequence, see below) showed homology to apple contig cg12357st_1428_21, built from 21 EST sequences (GenBank Acc: CN930585, CV525017, CN873920, EB149394, EB121634, EB116211, CN909797, EB115871, EB154300, CN877800, EB121026, CN932122, CN860924, EB110988, CO865849, CN488473, CN497072, CN903918, CN903403, DR996731 and CN894330). Contig cg12357st_1428_21 contains the complete coding sequence for a protein with similarity to ATP-dependent C1p protease proteolytic subunit (best BLASTX hit EEF49880, *Ricinus communis*, score 3 $e^{-128}$).

FRA8SE02HOH39 overlaps with the 3'-untranslated region of cg12357st_1428_21, and extends beyond the polyA tail into the non-transcribed genomic DNA as is shown in FIG. 4, panel B and the sequence alignment below.

Therefore, FRA8SE02HOH39 is an example of a genomic sequence containing the 3'-flanking sequences of a transcribed region.

Case 3.

Apple genomic sequence 02-H03 (sequence, see below) overlapped with the 5'-part of 40 apple ESTs, with similarity to an ethylene response factor (best BLASTX hit AAV66332, *Cucumis sativus*, score 6 $e^{-34}$). This is schematically shown in FIG. 4, panel C, for EST 91044950 (GenBank Acc: EB155368). The other ESTs had similar 5'ends. The alignment of a relevant part of the sequences is shown below. The genomic sequence extended 744 bp upstream of the translation start codon (ATG) of the gene. No sequence similarity was found to any gene outside the coding region in 02-H03, confirming that this is a genomic sequence. A conserved sequence, upstream of the transcription start is the TATA box. A putative TATA-box (TATAAA) was found 39 bp upstream of the start of the EST.

REFERENCES

Chang, S., Puryear, J. and Cairney J. 1993. A simple and efficient method for isolating RNA from pine trees. Plant Mol. Biol. Rep. 11: 113-116.

Kobayashi, N., Horikoshi, T., Katsuyama, H., Handa, T. and Takayanagi, K. 1998. A simple and efficient DNA extraction method for plants, especially woody plants. Plant Tissue Culture and Biotechnology 4: 76-80.

Sambrook, J., Fritsch, E. F. and Maniatis T. 1989. Molecular cloning. A laboratory manual. Second edition. Cold Spring Harbor Laboratory Press. USA.

FRA8S6E02IN5QW (SEQ ID NO: 13)
TATGTTGTGATAACCATATGGCTTCCCTGACATGCTCTGAACATACTCCC

ATGCTGCAGTAGAGTTGAATTTTGCACGCACCTCTGGATGCAAGGGAAGC

AAGGCTATTTGTGGATTAGAACTATCCTTGAGTGTCAACTCCCACCACTC

ATCCCATGGAATCACCGCTATAATTTCTTCACCCTGCAATATTAAATTAT

TAATAAATGTAAAAATCAACCAAAAAGAAAAGAACTAACCACAATAAACT

CTACAAAAAGAAAAGAACTAAAGCAAAGTTTAAAATAATTAAGAAATCT

GTGCAAGATTGTCATATATTTAATTTTGTCCCTAAACAAACGCTCATCAT

ATGTTCATCACTACAATCCTGATTCAACTATTATTCCACTAAAGGCAAAG

AACCAAAACATTTAGCTTAATTTCTATTCCTAATAAATCCCAAANACATG

AAATGAGTTGCTTGCATAAGCATATACTCAATTGAAAAT

FRA8S6E02HOH39

(SEQ ID NO: 14)
CAGCGACCTGTTTACGTGCAAGGTTTGGATGGAAGAGATTGAACAGTGAT

GCCAAATTGAATTGCCTCCAGAACAAATCTGAAGGGTGCAAAAAACATGT

ACTTTTTGAGAGTTGAAGAATGACGACACTTTCTTATGTTCTATATTATC

TTGGTTAAGTTTTTTGCAGGACGGAATGAATCCTCGTCTTTTTTTTCCCT

ATCAAAAAGAAGAAAGCTGAGTTTTTATGTTTGATGTCTTGATGATGGAT

GACCTAGTGTTCAAGTGAAAAATTCGACGGACAAAACGCTTGGCAATCCA

ATTTGTGCCGTGTATAATGTGTCACGTCCAAACGAGTTTCACATCGAAGA

AA

02_H03

(SEQ ID NO: 15)
tgttattgtttcattgaaacataacgttacataacaatataggnnncatt tggaacaacttttaaaatggctgaaaacgcattttgtgaaaatgatttt aaacagttttgagtaaaaatacaatgaatcatagaaaagtacttgaaatg ctttctacaaatagcatataactagtgcttatttcaaaaaatattnnnaa aacataaacaaaattctctaaaaatatttacggtcattgtaaaatcattt tcaaacgtgattataatcaggctatgtaaaatattctttaatattgactc aacaataaacggcgaatcgaaacgatacacggagtggagcgtgggagatg ggaggaaaggatcaccgcacgcaatcaaagagtgcattcgcagccgtcag atgatgataaaaatgatgggtgtgctctctcgacaacgcacacatgccac gtaatacggaaacgaacattgcacaattactaaattgccaccgatggaga gccgcccctccctaatcccatctcagtcaaatccctgttgactgtgcgc ctctctctctctctctctctctcctctctctttctctctcttcaattc ctcgctcatcatttctatataaacccacagcctgcctcctagtcctcca tcgccatctccacaccgtttctctcacatattttctgcagccaaacact cttttccacccaaacactacatacacaaaacgccaccgtttagttatggcg ccgagagagaagacggccaccgccgccgttaggatgaacggtaacggaaa cgtgaaggaggtgcattttagaggtgtgaggaagaggccgtggggaggt acgccgccgagatcaga Case 1. (SEQ ID NOS: 16-18)

```
                              *                                                              *    *
FRA8S6E02IN5QW                AGTTGAATCAGGATTGTAGTGATGAACATATGATGAGCGTTTGTTTAGGGACAAATTAAATATATGACAATCTTGCACAGATTTCT----TAATTATTT
AT1G70160                     CGAAGATTCGAGGTAGATGGGGTGGTTTTGAGACGTTAGAGAAATGGGTGACTGGGCTTTTGCTGGTCATACTGCTHTTTGTTTGAAGATGATTTGGG
                              *                                                     *                   *                 *
FRA8S6E02IN5QW                TAAACTTTGCTTAGTTCTTTTCTTTTTTGTAGAGTTTAT-TGTGTTAGTTCTTTCTTTTTTGGTTGATTTTTACATTTATTAATAATTAATATTGC-
AT1G70160                     GAATCTTTGGGTTGGTGTGAATCAGGACATGAGAACATGAGAACGTAAACATTTTGAGTAGTAGTGGATAGAGTTCTAATCCAAGATAGTTGGATAGAAGAGATATTTTACTATCTTTTTCC
                              INTRON/EXON                                                                                          *
FRA8S6E02IN5QW                ----AGGGTCAAGAGAAATATAGCGGTGAATCCAATGGGATGAGTGAGTGGTGGAGAGTTGACACTCCAAGATAGTTCTAATCCAAGATAGGCTTGCTTCCCTTGG
cg8984st_846_7                                                                                                                        GC
AT1G70160                     CCATAGAGGCAGTGATCCAAATCATTTCTTTGTTCTTGAACATCCCATCTGAACCCCCCTTGGGATGGAATGAATGATTTTTAGAAGAACAATCAANTCCCTCAAGTAGCTTTCCTTCCTTGGCATCAGCATA
```

Legend (alignment Case 1).
Alignment of apple genomic sequence FRA8S6E02IN5QW (SEQ ID NO: 18), apple EST contig cg8984st_846_7 (SEQ ID NO: 17) and Arabidopsis thaliana gene AT1G70160 (SEQ ID NO: 16). Only relevant parts of the sequences are shown. Matches in all three sequences are shown in dark grey, matches between two sequences are shown in light grey. Intron/exon boundaries are indicated and conserved intron boundary sequences AG and GT are bold. Asterisks above FRA8S6E02IN5QW indicate stop codons in the intron sequence in all three reading frames. Matches between FRA8S6E02IN5QW and AT1G70160 in this region are not indicated since homology in this region was low.

Case 2. (SEQ ID NOS: 19, 22)

```
FRA8S6E02HOH39A               CAGGCGACCTGTTTACGTGCAAGGTTTGGATGGAAGAGAATTCAACAGTGATGCCCAAATTGAAATTGCCTCCAGACAACAAATTCGAAGGGTGCAAAAAACATGT
CG12357ST_1428_21             CAGCCGACCTGTTTTACGTGCAAGGTTTGGATGGAAGAGAATTGAACACTGATGCCCAAATTGAAATTGCCTCCAGAACAAATTCGAAGGGTGCAAAAAACATGT
FRA8S6E02HOH39A               ACTTTTTTGAGAGTTGAAGAAATGACGACCACACTTTCTTATGTTCTTATATTGATGATGAACCTAGTGTTCAAGTGAAAAATTCGACGGACAAAACGCTTGGCAATCCA
CG12357ST_1428_21             ACTTTTTTGAGAGTTGAAGAAATGACGACCACACTTTCTTATGTTCTTATATTGATGATGAACCTAGTGTTCAAGTGAAAAATTCGACGGACAAAACGCTTGGCAATCCA
FRA8S6E02HOH39A               ATCAAAAGAAGAAGAAGCTGAGTTTTATGTTTTGATGATGATGACCTAGTGTTCAAGTGAAAAATTCGACGGACAAAACGCTTGGCAATCCA
CG12357ST_1428_21             ATCAAAAGAAGAAGAAGCTGAGTTTTATGTTTTTAAAAAAA
                                                                       polyA
FRA8S6E02HOH39A               ATTTGTGCCGTGTATAATGTGTCACGTCCAAACGAGTTTCACATCGAAGAAA
CG12357ST_1428_21
```

-continued

Legend (alignment case 2.)
Alignment of apple genomic sequence FRA8E02HOH39 (SEQ ID NO: 19) with apple EST contig cg12357st_1428_21 (SEQ ID NO: 22). Only relevant parts of the sequences are shown. Matches between the two sequences are shown in grey. The polyA-tail of the cDNA sequence is indicated. The genomic sequence extends beyond the 3'-untranslated region of the cDNA.

Case 3. (SEQ ID NOS: 20-21)

02_H03            AACAATAAACGGCGAATCGAAACGATACACGGAGTGGAGCGTGGGAGATGGGAGGAAAGGATCACCGCACGCAATCAAAGAGTGCATTCGCAGCCGTCAG

02_H03            ATGATGATAAAATGATGGGTGTGCTCTCGACAACGCACACATGCCACGTAATACGGAAACGAACATTGCACAATTACTAAATTGCCACCGATGGAGA

02_H03            GCCGCCCCTCCCTAATCCCATCTCAGTCAAATCCCTTGTTGACTGTGCGCCTCTCTCTCTCTCTCTCTCTCTCTCTCTTTCTCTTTCTCTTCAATTC

02_H03            CTCGCTCATCATTTCTATATAAAACCCACAGCCTGCCTCCTAGTCCTCCATCGCCATTCCACACCCCGTTTCTCTCACATATTTTCTGCAGCCAAACACT
gi|91044950                                                         CACCCGTTTCTCTCACATATTTTCTGCAGCCAAACACT

02_H03            CTTTCCACCCAAACACTACATACAAACACTACACAATACAAAAACGCCACCCGTTTAGTTATGGCGCCGAGGAGGAAGACCGGCCGCCGCGTTAGGATGAACGGTAACGGAAA
gi|91044950       CTTTCCACCCAAACACTACATATACAAAACGCCACCCGTTTAGTTATGGCGCCGAGGAGGAAGACCGGCCGCCGCGTTAGGATGAACGGTAACGGAAA

02_H03            CGTGAAGGAGGTGCATTTTTAGAGGTGTGAGGAAGAGGCCGTGGGGGAGGTACGCCGCCGAGATCAGA
gi|91044950       CGTGAAGGAGGTGCATTTTTAGAGGTGTGAGGAAGAGGCCGTGGGGGAGGTACGCCGCCGAGATCAGAGATCAGATCCCGGCAAGAAGAGCCGGGTCTGGCTCGGA (SEQ ID NO: 21).

Legend (alignment case 3.)
Alignment of apple genomic sequence 02_H03 (SEQ ID NO: 20) with apple EST gi|91044950 (GeneBank Acc : EB155368) (SEQ ID NO: 21). only relevant parts of the sequences are shown. Matches between the two sequences are shown in grey. A putative TATA-box in the genomic sequence is shown in bold (TATAAA). The start codon of the protein coding sequence is shown in bold (ATG).

The invention claimed is:

1. A method for the identification of genomic DNA in an organism, comprising
   a) providing a library of single stranded cDNA fragments that are coupled to beads through a linker that comprises an affinity ligand and a primer-recognition site;
   b) hybridizing single stranded genomic DNA (gDNA) fragments with said single stranded cDNA fragments, wherein said gDNA fragments comprise at least one adaptor to provide a primer recognition site, wherein the gDNA fragments are longer than the cDNA fragments,
   c) extending said hybrids with polymerase,
   d) amplifying said hybrids, and
   e) high throughput sequencing said hybrids,
   wherein said single stranded gDNA fragments have been obtained by isolating gDNA from an organism and preparing from said gDNA single stranded gDNA fragments ligated to adaptors, and
   wherein the single stranded cDNA fragments have been obtained by isolating mRNA from the same or a different organism and preparing from said RNA single stranded cDNA fragments with one adaptor containing an affinity ligand.

2. The method of claim 1, comprising the steps of:
   a) synthesizing cDNA from mRNA isolated from tissue samples of an organism as a template;
   b) fragmenting said cDNA to obtain cDNA fragments;
   c) polishing said cDNA fragments;
   d) ligating said cDNA fragments with a first adaptor comprising a recognition site for a rare cutter restriction enzyme and a second adaptor containing a biotin label;
   e) nick repairing said ligated cDNA fragments obtained in d);
   f) selecting said cDNA fragments obtained in e) that contain both first and second adaptors;
   g) amplifying the cDNA fragments obtained in f) using primers annealing to first and second adaptors, wherein one primer is complementary to the adaptor with a rare cutter restriction site and the other primer contains a biotin label to obtain amplified cDNA fragments;
   h) binding said amplified cDNA fragments of g) to streptavidin-coated affinity beads;
   i) removing from the bound cDNA fragments of h) adaptors containing the rare cutter restriction site using the corresponding restriction enzyme;
   j) removing any cDNA fragments not bound to said streptavidin affinity beads to obtain a bead-bound cDNA fragment library;
   k) fragmenting genomic DNA prepared from the same organism from which mRNA of a) was isolated to obtain gDNA fragments;
   l) ligating said gDNA fragments of k) with one single type of adaptor or with two different types of adaptors;
   m) melting said gDNA fragments of l) into single stranded gDNA fragments;
   n) hybridizing the single-stranded gDNA fragments from m) with the bead-bound cDNA fragment library of j) to obtain cDNA-gDNA hybrids;
   o) removing any unbound gDNA fragments by washing;
   p) extending the cDNA-gDNA hybrids by a polymerase to create double-stranded extended cDNA-gDNA hybrids;
   q) amplifying by PCR said extended gDNA-cDNA hybrids;
   r) selecting fragments larger than about 100 basepairs from said amplified extended gDNA-cDNA hybrids by size fractionation;
   s) high throughput sequencing the fragments obtained in r).

3. The method of claim 2 which further comprises
   t) comparing sequences of s) from two or more samples to identify polymorphisms.

4. The method of claim 2, which further comprises combining the sequences from s) into contigs of overlapping individual sequences.

5. The method of claim 4 which further includes annotating the contigs by automatic annotation.

6. The method of claim 2 which further includes annotating the sequences of s) by automatic annotation.

7. The method of claim 2 wherein the adaptor comprising a recognition site for a rare cutter restriction enzyme comprises the recognition site for the enzyme SapI.

8. The method of claim 2 wherein the fragmenting of b) is achieved by nebulisation.

9. The method of claim 1 wherein the sequences are obtained from individuals belonging to the same species and compared with EST data to reveal non-coding sequences.

10. The method of claim 1 wherein the sequences are obtained from one or more individuals belonging to different species and compared with EST data to reveal non-coding sequences.

11. The method of claim 1 wherein the sequences are obtained from two or more individuals belonging to the same species and compared to reveal polymorphic sites.

12. The method of claim 1 wherein the sequences are obtained from one or more individuals from different species and compared to reveal polymorphic sites.

13. The method of claim 1 wherein the sequences are obtained from one or more individuals from different species and compared to reveal conserved areas in genomic DNA.

14. The method of claim 1 which further comprises combining the sequences from step e) into contigs of overlapping individual sequences.

15. The method of claim 1 which further includes annotating the sequences from step e) by automatic annotation.

16. The method of claim 15 which further includes annotating the contigs by automatic annotation.

17. The method of claim 1 wherein said gDNA fragments comprise two adapters.

* * * * *